(12) United States Patent
Shamsi et al.

(10) Patent No.: US 8,168,440 B2
(45) Date of Patent: May 1, 2012

(54) POLYMERIC SULFATED SURFACTANTS FOR CAPILLARY ELECTROPHORESIS (CE) AND CE-MASS SPECTROMETRY (CE-MS)

(75) Inventors: Shahab Ahmed Shamsi, Tucker, GA (US); Syed Asad Ali Rizvi, Roswell, GA (US)

(73) Assignee: Georgia State University, Atlanta, GA (US)

( * ) Notice: Subject to any disclaimer, the term of this patent is extended or adjusted under 35 U.S.C. 154(b) by 1013 days.

(21) Appl. No.: 11/692,602

(22) Filed: Mar. 28, 2007

(65) Prior Publication Data

US 2007/0243622 A1    Oct. 18, 2007

Related U.S. Application Data

(60) Provisional application No. 60/743,858, filed on Mar. 28, 2006.

(51) Int. Cl.
G01N 30/72 (2006.01)
(52) U.S. Cl. ............. 436/173; 436/177; 436/178; 436/8
(58) Field of Classification Search ........................ None
See application file for complete search history.

(56) References Cited

U.S. PATENT DOCUMENTS

| | | | |
|---|---|---|---|
| 6,083,372 A | 7/2000 | Grover et al. | |
| 6,090,250 A | 7/2000 | Mazzeo et al. | |
| 6,270,640 B1 | 8/2001 | Warner et al. | |
| 6,849,722 B2 | 2/2005 | Warner et al. | |
| 2004/0084312 A1 | 5/2004 | Warner et al. | |
| 2006/0057659 A1 | 3/2006 | Bouvier et al. | |

FOREIGN PATENT DOCUMENTS

| | | |
|---|---|---|
| WO | 95/08529 A1 | 3/1995 |
| WO | 2005/099855 A1 | 10/2005 |
| WO | 2006/078859 A2 | 7/2006 |

OTHER PUBLICATIONS

Rizvi, Syed A. A. et al. "Polymeric alkenoxy amino acid surfactants: II. Chiral separations of beta-blockers with multiple stereogenic centers." Electrophoresis (2004) 25 853-860.*
Schulte, Georg et al. "Chiral capillary electrophoresis—electrospray mass spectrometry coupling with charged cyclodextrin derivatives as chiral selectors." Journal of Chromatography A (1998) 800 77-82.*
Akbay, et al., Copolymerized Polymeric Surfactants: Characterization and application in micellar electrokinetic chromatography, Electrophoresis 24(24): 4209-20 (2003).
Chu & Thomas, Photophysical Characterization of Polyelectrolytes in the Form of Polymerized Micelles from an Ionic Surfactant with a Terminal Double Bond, Macromolecules 24: 2212-16 (1991).
Karnissi, et al., Chiral Separations Using Polymeric Surfactants and Polyelectrolyte Multilayers in Open-tubular Capillary Electrochromatography, Anal. Chem. 75(22): 6097-6104 (2003).
Kapnissi, et al., Analytical Separations Using Molecular Micelles in Open-Tubular Capillary Electrochromatography, Anal. Chem. 74(10): 2328-2335 (2002).
Mazzeo, et al., A Resolution Equation for Electrokinetic Chromatography Based on Electrophoretic Mobilities, Anal. Chem. 67(17): 2966-2973 (1995).
Rizvi, et al., Polymeric Sulfated Amino Acid Surfactants: A Class of Versatile Chiral Selectors for Micellar Electrokinetic Chromatography (MEKC) and MEKC-MS, Anal. Chem. 79(3): 879-898 (2007).
Wang & Warner, Chiral Separations Using Micellar Electrokinetic Capillary Chromatography and a Polymerized Chiral Micelle, Anal. Chem. 66(21): 3773-76 (1994).
Edward & Shamsi, Chiral Separation of Polychlorinated Biphenyls Using a Combination of Hydroxypropyl Gamma-CD and a Polymeric Chiral Surfactant, Electrophoresis 23: 1320-27 (2002).
Lee & Shamsi, Chiral Separations of Anionic and Neutral Compounds Using a Hepta-Substituted Cationic Beta-Cyclodextrin as a Chiral Selector in Capillary Electrophoresis, Electrophoresis 23: 1314-19 (2002).
Shamsi, Micellar Electrokinetic Chromatography—Mass Spectrometry Using a Polymerized Chiral Micelle, Anal. Chem. 73: 5103-08 (2001).
Edward & Shamsi, Micellar Electrokinetic Chromatography of Polychlorinated Biphenyl Congeners Using a Polymerized Surfactant as the Pseudostationary Phase, J. Chromatogr. A. 903: 227-36 (2000).
Agnew, et al., Optimizing Enantioseparation of Phenylthiohydantoin Amino Acids with Polymerized Sodium-Undecanoyl-L-Valinate in Chiral Electrokinetic Chromatography, J. Liq. Chromatogr. Relat. Technol. 239: 1301-17 (2000).
Lee & Shamsi, Development of a Capillary Zone Electrophoresis Method for Separation of a Furan Combinatorial Library, Electrophoresis 21: 2405-11 (2000).
Thiami, et al., Capillary Electrochromatography of Cholesterol and its Ester Derivatives, Anal. Chem. 72: 2451-56 (2000).
Haynes, et al., Chiral Separation with dipeptide-terminated polymeric surfactants: The effect of an extra heteroatom on the polar head group, Electrophoresis 21(18): 1597-1605 (2000). Rugutt, et al., Enantiomers: Synthesis, NMR Spectroscopy, X-ray Crystallography, and Separation by Chiral Electrokinetic Chromatography Anal. Chem. 72: 3887-95 (2000).
Shamsi, et al., Molecular Micelles: Novel Pseudostationary Phases for CE, Am. Chem. Soc., Anal. Chem. 140A-149A (2001).
Rugutt, et al., A racemic strigol analogue at 100 K, Acta Crystallographica Section C; 759-761 (1999).
Macossay, et al., Synthesis of Polymerized N-Undecylenyl-L-Aminoacid and N-Undecylenyl-L-Peptide Derivatives, Tetrahedron Letters 40: 577-580 (1999).
Thibodeaux, et al., Separation and Identification of Chiral N-acylcalix[4]arene Amino Acid Derivatives by Use of Reversed-Phase HPLC, Chromatographia 49, No. 3/4, pp. 142-146, Feb. 1999.
Billiot, et al., Amino Acid Order in Polymeric Dipeptide Surfactants: Effect on Physical Properties and Enantioselectivity, Am. Chem. Soc., Anal. Chem. 71, 1252-1256 (1999).

(Continued)

*Primary Examiner* — Yelena G. Gakh
*Assistant Examiner* — Christopher A Hixson
(74) *Attorney, Agent, or Firm* — Sutherland Asbill & Brennan LLP

(57) ABSTRACT

The present invention relates generally to methods for enantiomeric separation of complex chemical mixtures using micelles of surfactant molecules that have a sulfate or sulfonate head group, a chiral selector, a linker, and a hydrophobic tail. Also provided are micelle compositions with sulfate or sulfonated head groups, methods of manufacture, and applications thereof. In particular, the micelles of the present invention provide an efficient enantiomeric separation and detection techniques for use in capillary electrophoresis and capillary electrophoresis with mass spectrometry.

7 Claims, 10 Drawing Sheets

OTHER PUBLICATIONS

Henry, et al., Separation of natural pyrethrum extracts using micellar electrokinetic chromatography, J. Chromatography A, 863, 89-103 (1999).

Yarabe, et al., Characterization and Thermodynamic Studies of the Interactions of Two Chiral Polymeric Surfactants with Model Substances: Phenylthiohydantoin Amino Acids, Am. Chem. Soc., Anal. Chem. 71, 3992-3999 (1999).

Shamsi, et al., Flavin mononucleotide for indirect laser-induced fluorescence detection of anions separated by capillary electrophoresis, J. Chromatography A, 835, 159-168 (1999).

Billiot, et al., Evaluating Chiral Separation Interactions by Use of Diastereomeric Polymeric dipeptide Surfactants, Am. Chem. Soc., Anal. Chem. 71, 4044-4049 (1999).

Shamsi, et al., Polysodium N-Undecanoyl-L-Leucylvalinate: A Versatile Chiral Selector for Micellar Electrokinetic Chromatography, Anal. Chem. 75, 379-387 (2003).

Tarus, et al., Counterions in Polymeric Amino Acid Based Surfactants: Effect on Physical Properties and Enantioselectivity, Am. Chem. Soc., Langmuir 19, 7173-7181 (2003).

Valle, et al., Combination of cyclodextrins and polymeric surfactants for chiral separations, Electrophoresis 25, 743-752 (2004).

Haddadian, et al., Separation of Saturated and Unsaturated Free Fatty Acids Using Capillary Electrophoresis with Indirect Photometric Detection, J. Chromatographic Science, 37, 103-107, Apr. 1999.

Haynes, et al., Polymeric Surfactants as Pseudostationary Phases for Separations in Electrokinetic Chromatography (EKC): A Review, Polymeric Surfactants in Electrokinetic Chromatography, vol. 18, No. 6, 317-382 (1999).

Norton, Dean, "Capillary electrochromatography—mass spectrometry of zwitterionic surfactants", Analytical Chemistry, pp. 6874-6886, vol. 77, No. 21, Nov. 1, 2005.

Cevdet Akbay, et al., "Simulataneous Enantioseparation and Tandem UV-MS Detection of Eight Beta-Blockers in Micellar Electrokinetc Chromatography Using a Chiral Moleculer Micelle", Analytical Chemistry, American Chemical Society, U.S. Jan. 1, 2005, vol. 77 No. 6 (Publised by American Chemical Society).

Shamsi, S.A., et al., "Polymeric Anionic Surfactant for Electrkinetic Chromatography: Separation of 16 Priority Polycyclic Aromatic Hydrocarbon Polluntants", Analytical Chemistry, American Chemical Society, U.S., Jul. 15, 1998, vol. 70. No. 14 (Published by American Chemical Society).

\* cited by examiner

POLYMERIC SULFATED SURFACTANTS FOR CAPILLARY ELECTROPHORESIS (CE) AND CE-MASS SPECTROMETRY (CE-MS)

RELATED APPLICATION DATA

The present application claims priority under 35 U.S.C. §119 to U.S. Provisional Application No. 60/743,858, entitled "Polymeric Sulfated Surfactants for Capillary Electrophoresis (CE) and CE-Mass Spectrometry (CE-MS)," filed on Mar. 28, 2006, the disclosure of which is incorporated herein by reference in its entirety.

FEDERALLY SPONSORED RESEARCH

This invention was made with government support under grant no. R01 GM 62314-02 awarded by the National Institute of Health. The government has certain rights in the invention.

FIELD OF THE INVENTION

The present invention relates generally to sulfated micelle compositions, methods of manufacture, and applications thereof. In particular, the micelles of the present invention provide an efficient enantiomeric separation and detection techniques for use in capillary electrophoresis and capillary electrophoresis with mass spectrometry.

BACKGROUND OF THE INVENTION

Stereochemistry, the study of three dimensional structure of molecules, is essential to the understanding organic chemistry, biochemistry, and biological systems. For example, biological systems are exquisitely selective and they often discriminate between molecules with subtle stereochemical differences. There are many forms of stereochemical differences such as structural isomers or constitutional isomers, wherein the isomers consist of the same molecular formula, but differ in their bonding sequences, i.e. the atoms are connected differently. Another form of stereochemical difference is known as stereoisomers, wherein the isomers have the same bonding sequence, but they differ in the orientation of their atoms in space. One form of stereoisomers is known as enantiomers. Enantiomers are pairs of compounds that are non-superimposable mirror images, which may also be referred to as chiral compounds. An analogous example of a chiral compound is the left and the right hand. The left and the right hand are mirror images but are non-superimposable on one another. Chiral compounds are important to many biological functions. Enzymatic reactions, drug metabolism, pharmaceutically active sites, and many other biological functions are only reactive to one isomer or enantiomeric form and inert or toxic the other form. Thus, in the pharmaceutical industry alone there is a strong need for an effective means to separate the stereoisomers.

The separation and detection of enantiomeric mixture or trace level enantiomeric impurity from the major enantiomer into individual optical isomers is one of the most challenging problems in analytical chemistry. This has important considerations in many areas of science, in particular the pharmaceutical and agricultural industries. For example, according to according to US Food and Drug Administration (FDA) and International Conference on Harmonization (ICH) Guidance for Industry Q3A Impurities in New Drug Substances, a chiral assay with a LOD of 0.1% enantiomeric impurity is mandatory for later stage of drug development. Separation of optical isomers is often very challenging due to the need of considerable time, effort, and expense.

High performance liquid chromatography and capillary electrophoresis are common techniques currently used to separate chiral compounds. Another separation technique includes reversible complexes formed of metal ions and chiral complexing agents, also known as ligand-exchange-chromatography. This technique involves multicomponent complexes containing a central metal ion and two chelating chiral molecules. The enantiomers are separated by using chiral mobile phase additives or by using a chiral stationary phase. Additionally, researchers have used micelles in chiral compound separation.

Micelles are typically surfactants. Micelles usually comprise both hydrophilic and hydrophobic groups which associate with one another in polar solvents such as water to form dynamic aggregates. A micelle typically takes roughly the shape of a sphere, a spheroid, an ellipsoid, or a rod, with the hydrophilic groups on the exterior and the hydrophobic groups on the interior. The hydrophobic interior provides, in effect, a hydrophobic liquid phase with solvation properties differing from those of the surrounding solvent. As a result, micelles have been used in applications of chiral recognition and separation. Chiral surfactants have been used to form micelles having distinct chiral properties. The resulting chiral microenvironment has been shown to exhibit selective interactions with different enantiomers in solution. However, micelle separation often results in heat, which could promote degradation in the compounds. Another disadvantage with traditional micelle chiral compound separation is that they have slow mass transfer rates and often times form troublesome emulsion systems. Conventional micelles include alkenoxy based amino acid surfactant with carboxylate head group, which often causes precipitation in solution at various pHs. This is mainly because the utility of alkenoxy amino acid-based surfactants is somewhat limited by the carboxylate head groups whose pH chemistry limits the electrophoretic mobility and solubility of the molecular micelles at pHs below 5.5.

Not only is separation of isomers important, but analysis and characterization of the isomers is equally important. The use of conventional chiral surfactant (above its critical micelle concentration) for capillary electrophoresis (CE) with mass spectrometry (MS) of optical isomers is not trivial. This is due to nonvolatility and high surface activity of the unpolymerized micelles. In addition, the use of low-molecular weight surfactant monomers provides a very unstable electrospray due to the large background signal generated from the dissociation of a micelle, which ultimately leads to the fouling of the ionization source and limits the sensitivity of the electrospray ionization-mass spectrometry (ESI-MS) applications. Finding a low molecular weight chiral selector that is MS-compatible is very difficult. Most applications concentrate on the use of partial-filling (PF)-CE-MS in which only part of the capillary is filled with micelle containing buffers. While this approach can be useful, it results in significant deterioration in chiral resolution.

Thus, there is a need for a more efficient and cost effective means for separation of optical isomers. In addition, because during the later stages of the drug development, sensitive analysis of the undesired optical isomer also is warranted. Thus, there is a continuing and growing need for improved separation and detection methods for chiral analysis.

SUMMARY OF THE INVENTION

It has been discovered that the sulfated amino acid-based polymeric surfactant of the present invention eliminates the use of surfactant above the critical micelle concentration ("CMC"). This is because polymeric surfactants have zero CMC, allowing lower concentrations to be used in micellar electrokinetic chromatography with mass spectrometry (MEKC-MS), which in turn not only reduces the undesired joule heating produced inside the capillary, but also significantly improves the MS detectability. Micelles form when the concentration of the amphophilic molecules in solution is greater than a characteristic value known as the critical micelle concentration ("CMC"). Because the individual surfactant monomers in a polymerized micelle must associate with one another, micelles form regardless of how low their concentration is. By contrast, with non-polymerized micelles the concentration of the surfactant must be higher than the CMC for a significant concentration of micelles to form. Furthermore, if the CMC of a charged surfactant is high, the high concentration of surfactant will generate considerable heat in micellar electrokinetic capillary chromatography (MECC), due to the high current resulting from the high charge density in solution. The heat generated can be deleterious to separations. By contrast, generation of heat with polymerized micelles can be greatly reduced because polymerized micelles have no CMC. Since MS detectors are considered a more sensitive and selective detection method than the conventional UV-detection, the development of CE-MS method based on sulfated molecular micelle should be applicable over a wide pH range for sensitive analysis of compounds important in pharmaceutical, agricultural and environmental industry. In one embodiment, a method for preparing sulfated micelle polymer is provided. In another embodiment, a more rugged and reliable CE-MS method for chiral analysis is provided. In yet another embodiment, the use of polymeric sulfated micelles developed for CE-MS analysis of chiral compounds in biological matrices (e.g., human urine) to conduct pharmacological and clinical and environmental studies that require the development of selective and sensitive chiral assays is provided.

Additionally, it has been discovered that the micelles of the present invention provide many unexpected results over the prior art. The present state-of-the-art in developing molecular micelles for MEKC-MS is limited to the use of amino acid based surfactants with carboxylate head groups. As mentioned earlier the use of these surfactants is somewhat limited to the basic pH range due to their poor water solubility in the acidic pH range of 1.5-5.0. In one embodiment, the MEKC-MS using the micelles of the present invention such as polymeric sulfated amino acid surfactants are provided for MEKC-UV analysis of several classes of acidic, basic, and neutral enantiomers. MEKC-MS and MEKC-UV utilizing the micelle of the present invention, e.g. sulfated molecular micelles, for chiral separations at low pH was found to be superior to high pH analysis. This points out the advantage of low pH separation of the investigated chiral analytes. In addition, analysis of pseudoephedrine spiked in human urine show superior MS detectability with limit of detection at least an order of magnitude better at low pH compared to high pH.

The micelle of the present invention is more rigid than the conventional unpolymerized micelles, a property that results in faster mass transfer. In addition, they have superior MS detectability compared to conventional micelles and even polymeric micelles (derived from carboxylate head group) at high pH. Additionally, the micelle of the present invention, e.g. polymeric sulfated amino acid surfactants, has no critical micelle concentration (CMC). During polymerization, the surfactant monomers associate with one another, micelles form regardless of surfactant concentrations. In contrast, the unpolymerized form of the similar amino acid sulfated micelle known in the art requires the surfactant concentration to be higher than the CMC for a significant concentration of micelle to form and to be effective as a separation media (without creating any significant heat) in CE. It has been discovered that the micelle of the present invention provides for CE and CE-MS at low pH (e.g. 2.0) using any monomeric (unpolymerized) or polymeric surfactants. It also has been discovered that the surfactants of the present invention provide for analysis of drugs in biological samples with high sensitivity. It also has been discovered that the micelles of the present invention, e.g. molecular sulfated micelles, are compatible with a variety of ionization sources (such as atmospheric pressure photoionization (APPI) and atmospheric pressure chemical ionization (APCI) in addition to conventional electrospray ionization (ESI)) for MEKC coupled to MS. Thus, a wide range of polar and non-polar compounds can be separated and detected. This includes not only chiral compounds, but also achiral hydrophobic neutral and charged compounds important in environmental sciences. In yet another embodiment, the micelles of the present invention can be used routinely for both qualitative and quantitative analysis for analysis of real world samples in both low and high pH ranges.

Objects and advantages of the invention will be set forth in part in the following description, or may be obvious from the description, or may be learned through practice of the invention. Unless otherwise defined, all technical and scientific terms and abbreviations used herein have the same meaning as commonly understood by one of ordinary skill in the art to which this invention pertains. Although methods and compositions similar or equivalent to those described herein can be used in the practice of the present invention, suitable methods and compositions are described without intending that any such methods and compositions limit the invention herein.

Figure 1:
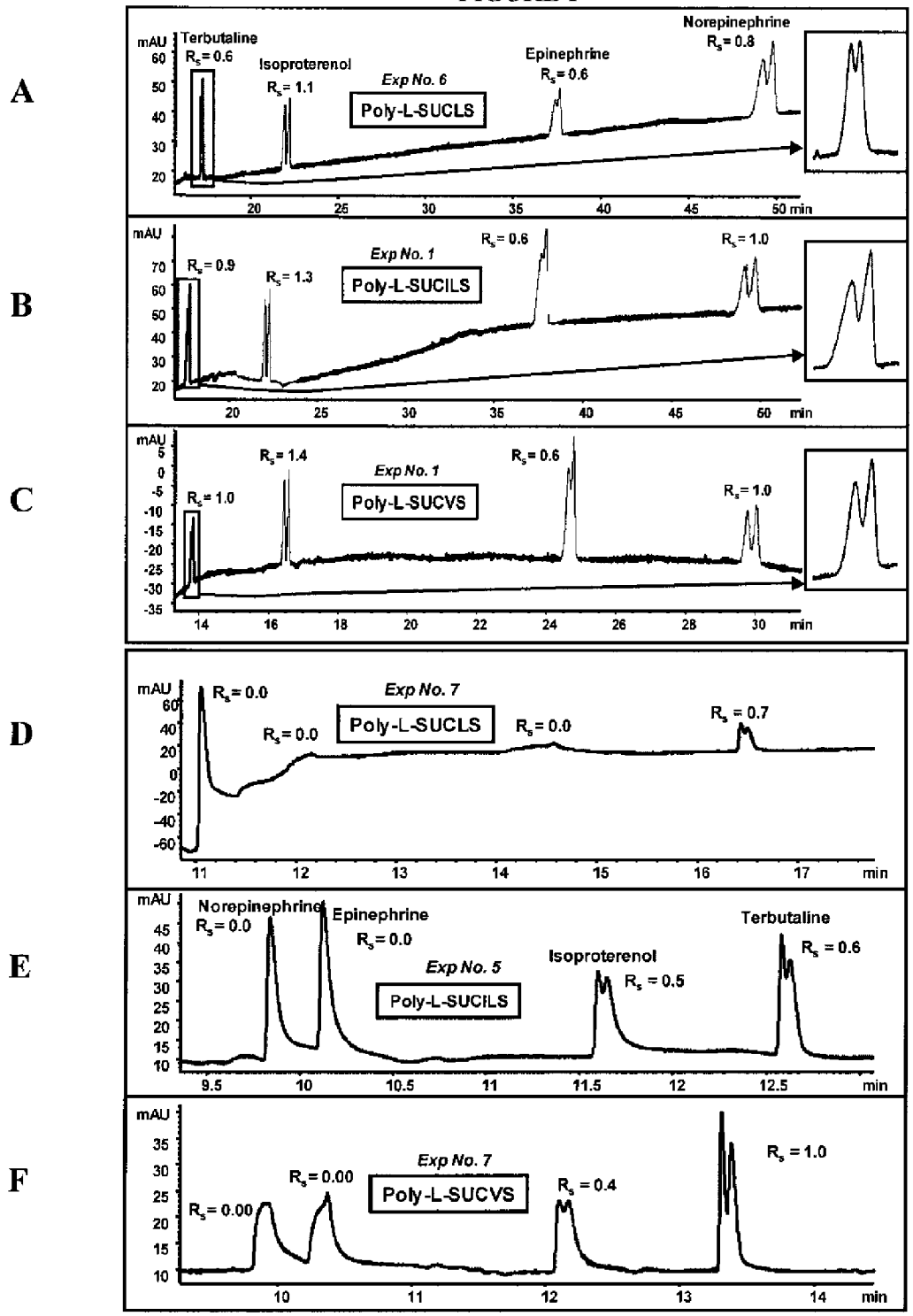
FIGS. 1A-1F illustrate chiral separation of positively charged analytes of phenylethylamines (class I) comprising two hydroxyl groups at low pH and moderately acidic to neutral pH using polymeric sulfated amino acid surfactants according to particular embodiments.

In describing the proffered embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DETAILED DESCRIPTION OF THE INVENTION

Reference now will be made in detail to the presently proffered embodiments of the invention. Each example is provided by way of explanation of embodiments of the invention, not limitation of the invention. In fact, it will be apparent to those skilled in the art that various modifications and variations can be made in the present invention without departing from the spirit or scope of the invention. For instance, features illustrated or described as part of one embodiment, can be used on another embodiment to yield a still further embodiment. Thus, it is intended that the present invention cover such modifications and variations within the scope of the appended claims and their equivalents.

Both separation and detectability of chiral compounds (i.e., mirror image compounds) can be enhanced through the use of polymeric surfactants also known as molecular micelles or micelle polymers. This is because polymeric surfactants eliminate much of the complex dynamic equilibrium associated with conventional micelles, and do not dissociate into individual surfactant monomers. In addition, polymerized chiral micelles have stronger chiral recognition properties and do not create any background for mass spectrometry detection (MS) than do otherwise identical, "conventional" or non-polymerized chiral micelles. Furthermore, the coupling of capillary electrophoresis (CE) with MS using conventional micelles above the critical micelle concentration is very difficult due to fouling of the ionization source in the electrospray ionization (ESI) interface when conventional micelles are used. In one embodiment, coupling of CE with MS for chiral separation using polymeric micelles or surfactants is provided. In another embodiment, the micelle polymers of the present invention provide better signal-to-noise ratio, low volatility and less spectral clutter in the low mass region when employed as pseudostationary phase. Thus, the polymeric surfactants provided exhibit efficient separation and detection of chiral compounds.

In one embodiment, polymeric sulfated amino acid micelles with sulfated head group to be used in analytical separations coupled with either UV or MS detection of separated chiral molecules are provided.

In another embodiment, the separation and detection of enantiomeric mixture or trace level enantiomeric impurity from the major enantiomer into individual optical isomers is provided.

In one embodiment, the polymeric sulfated amino acid surfactants provided can be employed at any pH in analytical separations without any problem of precipitation in solution. Non-limiting examples of the pH range may be from about 1.5 to about 12.5. It should be noted that a variety of pharmaceutical drugs are cationic and they are best enantioseparated in the acidic pH range of 2.5-4.0. Also, it is expected that the peak-tailing problem associated with the separation of cationic chiral compounds at elevated pH could be overcome, by achieving the same separation at low pH. Thus, in one embodiment, the design of a pH independent molecular micelle with sulfate head groups that could function as a chiral pseudostationary phase with enhanced MS detectability over a broad pH range has been provided. Without being bounded to theory, the use of acidic micellar electrokinetic chromatography (MEKC) buffers in the pH range of 1.5-3.0 could render weakly or moderately acidic anionic compounds neutral. Hence, enantioseparation of such compounds also is feasible due to a decrease in electrostatic repulsion with the negatively charged sulfated micelles, which in turn should improve the enantioselectivity.

Polymeric Sulfated Amino Acid Surfactants

In one embodiment, chiral micelles suitable for the present invention include the micelle represented by the compound of formula I:

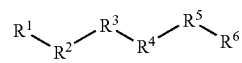

I wherein $R^1$ is an optional functionality group, $R^2$ is a hydrophobic tail, $R^3$ is a linker, $R^4$ is a chiral selector, $R^5$ is a head, and $R^6$ is a counterion.

In another embodiment, the chiral surfactants or micelles suitable for the present invention include chiral anionic surfactant or micelle as represented by the compound of formula II:

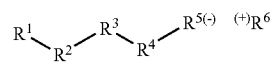

II wherein $R^1$ is an optional functionality group, $R^2$ is a hydrophobic tail, $R^3$ is a linker, $R^4$ is a chiral selector, $R^5$ is a head, and $R^6$ is a counterion.

In another embodiment, the chiral surfactants or micelles suitable for the present invention include chiral cationic surfactant or micelle as represented by the compound of formula III,

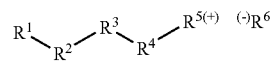

III wherein $R^1$ is an optional functionality group, $R^2$ is a hydrophobic tail, $R^3$ is a linker, $R^4$ is a chiral selector, $R^5$ is a head, and $R^6$ is a counterion. As used herein the terms "micelle" and "surfactant" are synonymous.

As used herein, the phrase "optional functionality group" may be any functional group which does not materially affect the efficacy of the micelles. Non-limiting examples of the optional functionality group include substituted or unsubstituted alkenyl or alkynyl groups. In one embodiment, the optional functionality group may be polymerized with at least one other micelle.

As used herein, the phrase "hydrophobic tail" consists of a $C_6$ to $C_{18}$ carbon chain. The carbon chain may be saturated or unsaturated, straight, branched, or cyclic, primary, secondary, or tertiary hydrocarbon. The hydrophobic tail group optionally can be substituted with one or more moieties selected from the group consisting of hydroxyl, carboxy, carboxamido, carboalkoxy, acyl, amino, alkylamino, halo, aryl, heteroaryl, heterocyclic, arylamino, alkynl, alkenyl, alkoxy, aryloxy, nitro, cyano, sulfo, sulfato, phosphor phosphato, and phosphonato.

As used herein, the phrase "linker" represents any functional group capable of linking at least one hydrophobic tail with at least one chiral selector group. Non-limiting examples of linker includes amide, carbamate, and ureido.

As used herein, the phrase "chiral selector" represents amino acid, amino acid derivatives, or any other chiral center-bearing molecule. Suitable amino acids for use in embodiments of this invention include, but are not limited to, aspartic acid, arginine, glycine, glutamic acid, proline, threonine, threonine, cysteine, cystine, alanine, valine, phenylalanine, tyrosine, leucine, isoleucine, asparagine, serine, lysine, histidine, tryptophan, ornithine, methionine, carnitine, aminobutyric acid, glutamine, hydroxyproline, taurine, norvaline, sarcosine, and amino methanesulfonic acid. The amino acid or amino acid derivative also may be in the D- or L-configuration and in the mono-, di-, or tri-form. Additionally, the amino acid or amino acid derivative may be of $\alpha$-, $\beta$-, $\gamma$-, $\delta$-, or $\epsilon$-configuration if appropriate. The amino acid or amino acid derivative may be natural or synthetic. The amino acid or amino acid derivative also may be modified. A modified amino acid or amino acid derivative refers to any amino acid wherein at least one atom has been added, removed, substituted, or combinations thereof, e.g. N-alkyl amino acid or N-acyl amino acid. As used herein, amino acids encompass both modified and unmodified amino acids.

As used herein, the term "head" refers to a group with a positive or negative charge that exhibits any properties of water solubility. Non-limiting examples of head groups suitable for the embodiments of the present invention include sulfonates and sulfates.

As used herein, the phrase "counter ion" refers to any group which can stabilize the head. Non-limiting examples of counter ion suitable for the embodiments of the present invention include alkali, alkaline earth or transition metals (e.g., $Li^+$, $Na^+$, $K^+$, $Rb^+$, $Cs^+$, $Mg^+$, $NH_4^+$, $Cu^{+2}$, $Zn^{2+}$, etc.), organic counter ions (e.g., $(CH_3)_4N^+$, $(C_2H_5)_4N^+$, $(C_3H_7)_4N^+$, $(C_4H_9)_4N^+$), and quaternary ammonium.

The term "alkyl", as used herein, unless otherwise specified, refers to a saturated or unsaturated, straight, branched, or cyclic, primary, secondary, or tertiary hydrocarbon, typically of $C_1$ to $C_{18}$. The alkyl group optionally can be substituted with one or more moieties selected from the group consisting of hydroxyl, carboxy, carboxamido, carboalkoxy, acyl, amino, alkylamino, halo, aryl, heteroaryl, heterocyclic, arylamino, alkynl, alkenyl, alkoxy, aryloxy, nitro, cyano, sulfo, sulfato, phospho, phosphate, and phosphonato.

The term "alkenyl", as referred to herein, and unless otherwise specified, refers to a straight, branched, or cyclic hydrocarbon of $C_2$ to $C_{10}$ with at least one double bond. The alkenyl groups optionally can be substituted in the same manner as described above for the alkyl groups, and also optionally can be substituted with a substituted or unsubstituted alkyl group.

The term "alkynyl", as referred to herein, and unless otherwise specified, refers to a $C_2$ to $C_{10}$ straight or branched hydrocarbon with at least one triple bond. The alkynyl groups optionally can be substituted in the same manner as described above for the alkyl groups, and also optionally can be substituted with a substituted or unsubstituted alkyl group.

The term "aryl", as used herein, and unless otherwise specified, refers to phenyl, biphenyl, or naphthyl, and preferably phenyl. The aryl group optionally can be substituted in the same manner as described above for the alkyl groups, and also optionally can be substituted with a substituted or unsubstituted alkyl group.

The term "heteroaryl" or "heteroaromatic", as used herein, refers to an aromatic or unsaturated cyclic moiety that includes at least one sulfur, oxygen, nitrogen, or phosphorus in the aromatic ring. Non-limiting examples include furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, pyridazinyl, pyrazinyl, cinnolinyl, phthalazinyl, quinoxalinyl, xanthinyl, hypoxanthinyl, and pteridinyl. The heteroaryl or heteroaromatic group optionally can be substituted in the same manner as described above for the alkyl groups, and also optionally can be substituted with a substituted or unsubstituted alkyl group.

The term "heterocyclic" refers to a saturated non-aromatic cyclic group which may be substituted, and wherein there is at least one heteroatom, such as oxygen, sulfur, nitrogen, or phosphorus in the ring. The heterocyclic group optionally can be substituted in the same manner as described above for the alkyl groups, and also optionally can be substituted with a substituted or unsubstituted alkyl group.

The term "aralkyl", as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above. The aralkyl or alkaryl group optionally can be substituted in the same manner as described above for the alkyl groups, and also optionally can be substituted with a substituted or unsubstituted alkyl group.

The term "halo", as used herein, specifically includes chloro, bromo, iodo, and fluoro.

The term "alkoxy", as used herein, and unless otherwise specified, refers to a moiety of the structure —O-alkyl, wherein alkyl is as defined above.

The term "acyl", as used herein, refers to a group of the formula C(O)R', wherein R' is an alkyl, aryl, alkaryl or aralkyl group, or substituted alkyl, aryl, aralkyl or alkaryl, wherein these groups are as defined above.

It is appreciated that one of ordinary skill in the art may synthesize the micelles of the present invention in any known manner.

In one embodiment, a non-limiting example for the synthesis of chiral sulfated surfactant with a carbamate or ureido linkage is provided. The synthesis of sulfated surfactants begins with the conversion of a terminally unsaturated amine or alcohol to the isocyanate or chloroformate, respectively, as seen in Scheme 1. These products then can be made to react with chiral amino alcohol and the respective products can be converted to sulfated surfactants by reacting with chlorosulfonic acid and pyridine. After 1 hour of the reaction, a sufficient amount of concentrated HCl is added to decrease the pH ~1. This is followed by extraction with dichloromethane. The dichloromethane layer (i.e., bottom layer) is washed with water, dried over sodium sulfate, and concentrated in vacuo to yield the acidic form of the surfactant, which is subsequently converted into a sodium salt form with equimolar $NaHCO_3$. These surfactants then are lyophilized and the resulting white powder is stored in a moisture free environment (e.g., desiccators). The polymerizable double or triple bond may be located at the terminal end of the monomeric surfactant, which upon polymerization with $^{60}Co$ γ-irradiation yields micelle polymers.

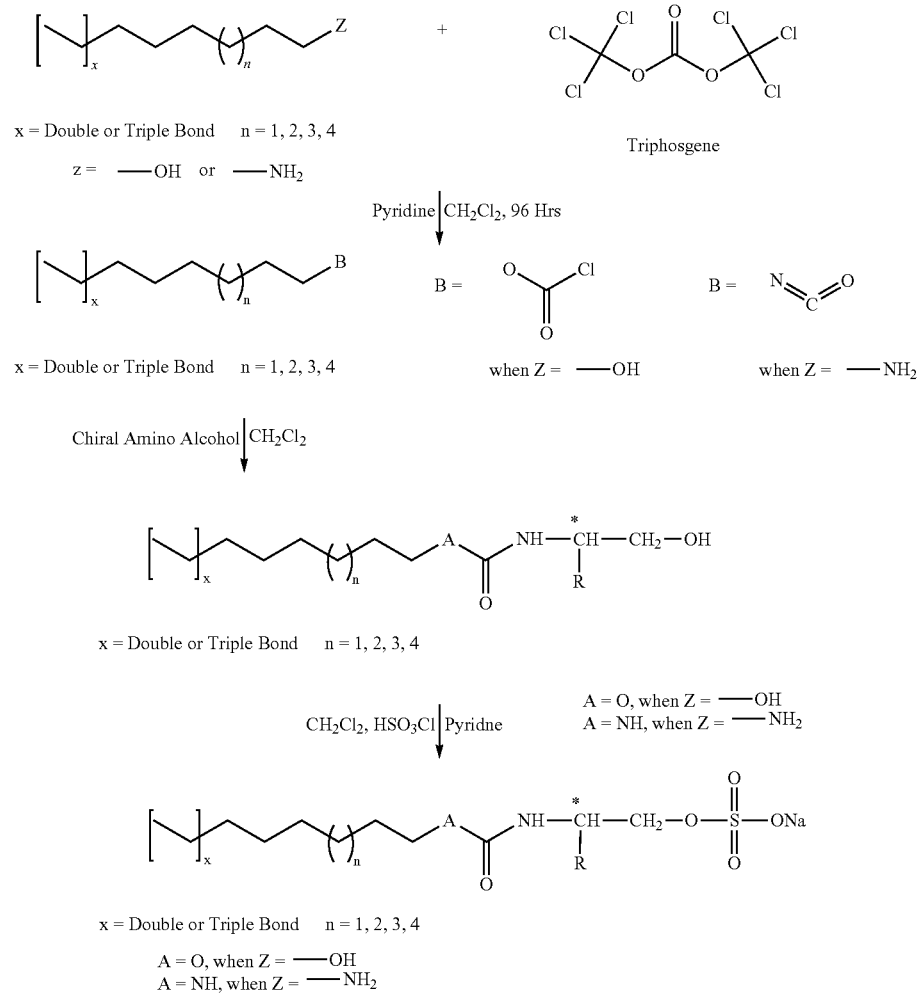

In another embodiment, a non-limiting example of the synthesis of the chiral sulfated surfactants with amide linkage is provided, as illustrated in Scheme 2. The amide linked sulfated surfactants can be synthesized conveniently by converting the unsaturated carboxylic acid into N-hydroxy succinimide ester. This ester then is made to react with a chiral amino alcohol and the resulting product is converted to a sulfated surfactant by a reaction with chlorosulfonic acid and pyridine. After 1 hour of the reaction, a sufficient amount of concentrated HCl is added to decrease the pH ~1 and extracted with dichloromethane. The dichloromethane layer (bottom) is washed with water, dried over sodium sulfate, and concentrated in vacuo to yield the acidic form of the surfactant, which subsequently is converted into a sodium salt form with equimolar $NaHCO_3$. These surfactants then are lyophilized and the resulting white powder is stored in a moisture free environment (e.g., desiccators). Polymerization of amide surfactants is achieved by a $^{60}$Co γ-irradiation source (1.3 Mrad/hr), for 36 hours.

Scheme II

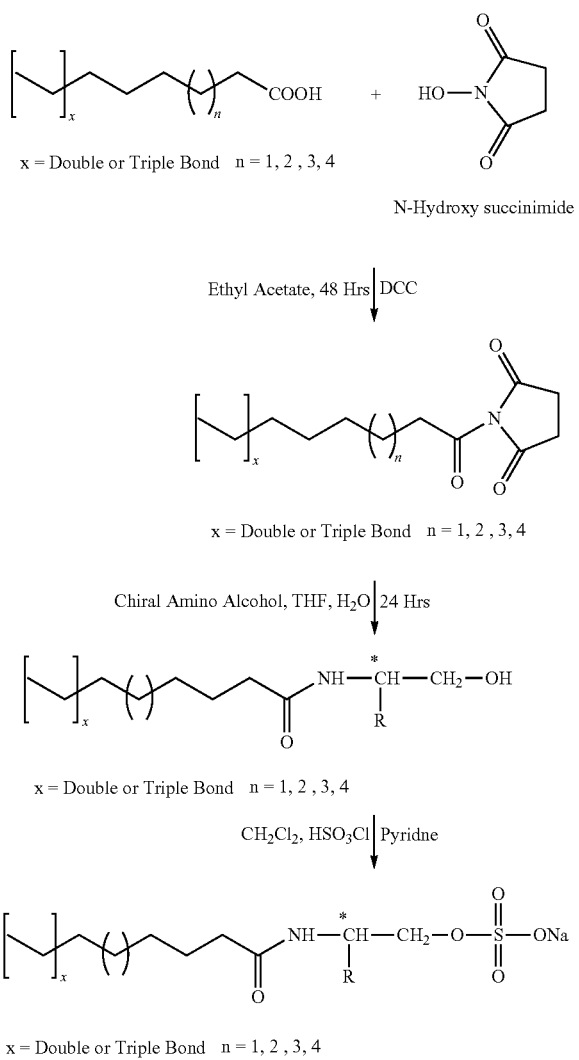

wherein R in Scheme 2 is alkyl side chain of the following amino acid:

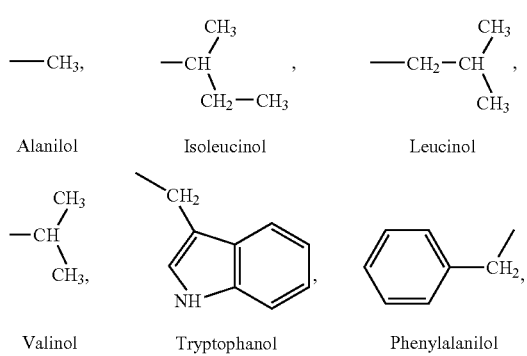

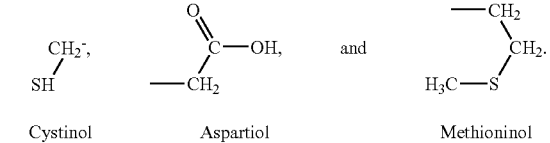

The synthetic scheme outlined above is a fairly general one in which the steps may be modified to obtain a micelle with different groups. It is appreciated that the micelle may be polymerized in any manner known to those skilled in the art. Schemes I and II are only illustrative, as one skilled in the art may modify any variable of the synthetic routes. For example, one of ordinary skill in the art may modify the synthetic route using any reagent or solvent known in the art which will not materially affect the formation of the micelle. Additionally, the synthetic reaction may be carried out at any temperature, pressure, pH, or reaction time provided that the modification does not materially affect the resulting micelle.

The synthesized micelles may be characterized via any known techniques known to those skilled in the art. Non-limiting examples of techniques for the characterization of synthesized micelles include surface tensiometer, optical rotation, fluorescence spectroscopy, NMR spectroscopy and density measurements.

Applications and Uses of Polymeric Sulfated Amino Acid Surfactants

The micelles of the present invention, such as for example, sulfated amino acid polymeric surfactants can be employed at any pH. In one embodiment, the micelles provided may be utilized for chiral separation at a pH from about 1.5 to about 12.5. In another embodiment, the micelles provided may be utilized for chiral separation at a pH from about 1.5 to about 5.5. In still another embodiment, the micelles provided may be utilized for chiral separation at a pH of about 2 to about 3.

In one embodiment, the micelles embodied herein may provide chiral separation of negatively charged analytes. In general, negatively charged racemic analytes poorly interact with the negatively charged chiral micelle, resulting in either low or no chiral separation. Those skilled in the art appreciate that these problems can be overcome by employing low pH run buffer; however, low pH's generally create additional problems due to the low solubility of negatively charged micelle, particularly micelles bearing carboxylate head groups. Thus, in one embodiment, the micelles provided herein may be utilized at any suitable pH. In particular, the micelles embodied herein may be used at a low pH (e.g., about 2 to about 3) in which many moderately or weakly acidic analytes are neutral.

In another embodiment, the micelles embodied herein may provide chiral separation of neutral analytes. Chiral separation of neutral analytes generally occurs at an elevated pH because of the difficulty of performing separation using molecular micelles at a low pH.

In another embodiment, the micelles embodied herein may provide chiral separation and detection of positively charged analytes (e.g. phenylethyl amines). As described in the examples provided hereinbelow, two classes of phenylethylamines, one with two hydroxyl groups and the other with one hydroxyl group may be resolved at a low pH with sulfated polymeric surfactants as compared to a high pH with carboxylated polymeric surfactants.

In another embodiment, the micelles embodied herein may provide enantiomeric analysis of abused drugs. Such procedures are important in forensic laboratories which can provide data resulting from enantiomeric analysis. Such data may (a) provide information for sentencing guidance for certain drug-related offenses; (b) assist in drug-related investigations; and (c) determine whether the drug of concern is derived from a controlled substance. For example, ephedrine and pseudoephedrine (ψ-ephedrine) are common over-the-counter (OTC) pharmaceuticals. They also are frequently used as adulterants in packaging drugs of abuse. Similarly, (−)-ephedrine has been a popular precursor for illicit manufacturing of (+)-methamphetamine. Typically, the ephedra plant material extracts (−)-ephedrine and (+)-ψ-ephedrine are used for conversion to methamphetamine in these illicit manufacturing processes. Thus, the identification of ephedrine and ψ-ephedrine, and their enantiomeric composition in methamphetamine samples, may help identify the drug's precursor material and provide valuable information to the investigation process.

In yet another embodiment, the micelles embodied herein may provide analytical tools for the detection of drug identification. For example, a significant analytical concern is of the reported false methamphetamine identification in urine specimens due to excessive consumption of ephedrine and ψ-ephedrine. Coupling of chiral CE with mass spectrometry (MS) provides important information about not only the amount of drug in the urine, but also the structure of the separated compounds. Such uses of CE-MS are particularly beneficial for the separation and structure confirmation of metabolites in forensic analysis, as described hereinabove. Thus, in one embodiment chiral analysis of ψ-ephedrine enantiomers with CE-MS using polymeric sulfated amino acid surfactants at a low pH is provided. Accordingly, the polymeric sulfated amino acid surfactants provided herein may be used for sensitive analysis of nasal decongestants (e.g., pseudoephedrine) in human urine with a limit of detection at least an order of magnitude lower than that of MS detection at high pH.

In still another embodiment, the polymeric sulfated micelles embodied herein may be used for chiral separation using open-tubular capillary electrochromatography (OT-CEC). Conventional forms of capillary electrochromatography (CEC) use a fused-silica capillary with a typical internal diameter of 50-100 μm, packed with a typical HPLC stationary phase; however, Several problems prevent conventional CEC from being a viable alternative to CE or high performance liquid chromatography (HPLC). For example, conventional CEC requires fabrication of frits to retain the packed particles within the column. In addition, packed capillaries tend to form bubbles around the packing material or at the frit. Thus, OT-CEC provides an alternative approach to conventional CEC, avoiding many of the problems associated with conventional CEC. In OT-CEC, a stable coating is constructed on the inner walls of a capillary to provide efficient chromatographic separations and reproducible EOF. Desirably, the coating comprises a polyelectrolyte multilayer (PEM) that is constructed in situ using a layer-by-layer deposition process of alternating rinses of positively and negatively charged polymers, wherein the negatively charged polymer comprises the polymeric sulfated micelles embodied herein. Procedures for preparing PEM coatings are well known to those of ordinary skill in the art and are described in more detail by Kapnissi, et al. in *Anal. Chem.* 74, 2328-2335 (2002) and *Anal Chem.* 75, 6097-6104 (2003), the disclosures of which are incorporated herein by reference in their entirety.

The two separation methods commonly interfaced to atmospheric pressure ionization mass spectrometry (API-MS) are high performance liquid chromatography (HPLC) and capillary electrophoresis (CE), both of which provide high separation efficiency for the analysis of nonvolatile compounds. High separation efficiency are required in both HPLC-MS and CE-MS in particular for the separation of isomers (e.g., geometrical and optical isomers) that have the same molecular weight. Separation of isomers is therefore important, whereas mass spectrometry can provide sensitive detection and structural information of the separated isomers in both HPLC and CE. Although the use of MS as a detector for reversed phase HPLC is possible, most of the enantioselective LC methods require bonded or coated chiral stationary phases (CSPs) and normal-phase solvents such as n-hexane and n-heptane as mobile phases. It is well-known that the use of these solvents pose an explosion hazard for API-MS. To overcome the incompatibility of the normal phase solvents for API-MS post-column addition of MS compatible solvents have been proposed. However, the post-column method reduces both detection sensitivity in MS and chromatographic resolution in HPLC.

There are several general advantages in using micellar electrokinetic chromatography (MEKC)-MS over HPLC-MS. For example, the advantages include; (i) combination of electrophoretic and chromatographic mechanism in MEKC-MS results in higher selectivity and efficiency compared to HPLC-MS; (ii) mobile phase flow rates in MEKC-MS (sub μL/min) are more compatible to API-MS, which in turn also reduces the consumption of toxic organic solvents; (iii) radiolabelling of the chiral/achiral molecules with same molecular weight is not necessary due to higher separation efficiency and high selectivity in MEKC; (iv) the use of polymeric surfactant provides a rugged and reproducible electroosmotic flow, thus data is very reproducible and expeditiously obtained in MEKC-MS; and (vi) the cost for making micelles for MEKC-MS is much lower than HPLC-MS, since only small amount of surfactant is required in MEKC to achieve higher efficiency separation with sensitive MS detection. In contrast, HPLC requires gram quantity of stationary phases to pack in the column. In addition, the lower cost of MEKC also enables wider selection of exotic surfactant to improve the separation power.

There are several advantages in using MEKC-MS over CZE-MS. Capillary zone electrophoresis (CZE)-MS utilizes nonvolatile moving chiral selectors (e.g., cyclodextrins, vancomycin, or non-polymerized surfactants) that results in fouling of the ionization sources of the API-MS due to chemical noise producing ions that add to the mass spectral background. In MEKC-MS the use of molecular micelles produces relatively less spectral background. Both neutral and charged compounds can be separated with MEKC-MS whereas CZE-MS only separates charged compounds.

Reference now will be made in detail to the presently proffered embodiments of the invention. Each example is provided by way of explanation of embodiments of the invention, not limitation of the invention. In fact, it will be apparent to those skilled in the art that various modifications and variations can be made in the present invention without departing from the spirit or scope of the invention. For instance, features illustrated or described as part of one embodiment, can be used on another embodiment to yield a still further embodiment. Thus, it is intended that the present invention cover such modifications and variations within the scope of the appended claims and their equivalents.

EXAMPLES

The characterization and ability of chiral sulfated surfactants to separate complex chemical mixtures was determined in the examples provided hereinbelow. These results were published by Rizvi, et al. in *Anal. Chem.* 79, 879-98 (2007), the disclosure of which is incorporated herein by reference in its entirety.

Example 1

Characterization of the Physiochemical Properties of Monomers and Polymers of Sodium N-Undecenoxycarbonyl-L-amino Acid Sulfates (L-SUCAAS)

The physiochemical properties of the enantiomerically pure, synthetic sulfated amino acid surfactants sodium N-undecenoxycarbonyl-L-leucine sulfate (L-SUCLS), sodium N-undecenoxycarbonyl-L-isoleucine sulfate (L-SUCILS), and sodium N-undecenoxycarbonyl-L-valine sulfate (L-SUCVS) and their respective micelle polymers (poly-L-SUCLS, poly-L-SUCILS, and poly-L-SUCVS, respectively, collectively referred to as polysodium N-undecenoxycarbonyl-L-amino acid sulfates (poly-L-SUCAAS)) were determined and are summarized in Table 1.

Determination of CMC

The critical micelle concentration (CMC) was determined using a sigma 703 Digital Tensiometer (KVS Instruments USA, Monroe, Conn.), by the Du NoÜy ring method at room temperature. In this method, a platinum ring with defined geometry was immersed into a liquid and then carefully detached through the liquid surface. The digital readout displayed a peak value of force/length (mN/cm), which was the surface tension of the liquid sample. Solutions of various concentrations (between 5 mM-75 mM) were prepared and their surface tensions were measured. The surface tension (mN/cm) was plotted against the surfactant concentration (mM). At the points in which there was no appreciable change in surface tension, the CMC was determined from the inflection point, which was estimated by taking the point of intersection of two linear lines.

Optical Rotation Measurement

The optical rotation data of both monomers and polymers of the synthesized chiral sulfated surfactants were obtained by an AUTOPOL III automatic polarimeter (Rudolph Research Analytical, Flanders, N.J.), by measuring the optical rotation of a 1% (w/v) solution in triply deionized water. All measurements were made at room temperature (25° C.) at a wavelength of 589 mm.

Fluorescence Measurements (Aggregation Number)

Fluorescence measurements were obtained on a PTI QauntaMaster luminescence spectrometer (Model QM-1) (Photon Technology International, Ontario, CA) at room temperature. The aggregation number (A) of the monomer and the molecular micelles of the synthesized chiral sulfated surfactants were determined by the fluorescence quenching method using the equation:

$$\ln(I_0/I) = \{A[Q]\}/\{[S_{tot}] - CMC\}$$

wherein $I_0$ and I are the fluorescence intensities of the pyrene-surfactant mixture without and with quencher, respectively, A is the aggregation number, [Q] is the quencher concentration, $S_{tot}$ is the total surfactant concentration, and CMC is the critical micelle concentration of the surfactant. The excitation and emission wavelengths were set at 335 nm and 393 nm, respectively. Pyrene and cetylpyridinium chloride (CPyrCl) were used as the fluorescent probe and the quencher, respectively. A $1.0 \times 10^{-3}$ M stock solution of pyrene was prepared in methanol. A $2.0 \times 10^{-3}$ M stock solution of the quencher and $1 \times 10^{-1}$ M solution of polymers and monomers of synthesized chiral sulfated surfactants were prepared separately in triply deionized water. A known volume of the probe stock solution was pipetted in a clean volumetric flask, a gentle stream of nitrogen gas was used to evaporate the methanol, and an aqueous surfactant solution was added. The concentrations of the probe and the surfactant were $2.0 \times 10^{-6}$ M and $1.0 \times 10^{-1}$ M, respectively (solution 1). Solution 1 was sonicated for 90 minutes, stored in a dark area, and left to equilibrate overnight. The equilibrated solution was divided in two portions. The first portion was diluted with deionized water to provide a $1.0 \times 10^{-6}$ M probe and $5 \times 10^{-2}$ M surfactant (solution 2), while the second portion was mixed with quencher stock solution to make a solution containing $1.0 \times 10^{-3}$ M quencher, $1.0 \times 10^{-6}$ M probe, and $5 \times 10^{-2}$ M surfactant (quencher solution). The quencher solution was added to solution 2 in increasing volume increments of 50 µL and allowed to equilibrate for 20 minutes before fluorescence measurements were taken. The decrease in emission spectra of the probe was recorded after addition of each aliquot of the quencher solution and the logarithm of the intensity ratio ($I_0/I$) was plotted against the quencher concentration. A was obtained from the slope of the plot of ln ($I_0/I$) vs[Q] (where A=slope×$[S_{tot}]$−CMC).

Polarity Measurements

The polarity of the aggregated surfactant core was measured using a fluorescence molecule (e.g., pyrene) that stays in the core and is sensitive to the polarity of the environment. The emission spectrum of the pyrene molecule, which was sensitive to the environment in which it was dissolved, consisted of five vibronic bands. The intensities of these vibronic bands depended on the polarity of the environment in which pyrene was dissolved. The polarities of the monomers and polymers of the synthesized chiral sulfated surfactants were determined by recording the emission spectra of pyrene-surfactant solution from 360 nm to 400 nm. The ratio of the intensity of band I to band III ($I_1/I_3$) of pyrene was used to determine the polarity. An increase in the intensity of the band I was accompanied by a decrease in the intensity of the band III as the polarity of the environment was increased.

Determination of Partial Specific Volume (Density Measurements)

The partial specific volume (v) often is used for the characterization of substances of interest due to the difficulty of measuring the exact volume of a particle. Accordingly, the v was measured by plotting the inverse of the density (1/ρ) of the aqueous surfactant solution versus the weight fraction (W) of the surfactant using the equation:

$$1/\rho = v + W \partial(1/\rho)/\partial W$$

wherein W is defined by the expression:

$$W = m_w/(m_w + m_s)$$

wherein $m_w$ and $m_s$ represent the masses of water and the surfactant, respectively. Seven different surfactant solutions (5 mM, 10 mM, 20 mM, 40 mM, 60 mM, 80 mM, and 100 mM) were prepared in triply deionized water for density measurements. The v of all surfactant systems used in this study were obtained as the y-intercept of the 1/ρ vs. W plots.

A high-precision digital densitometer, model DMA 4500/5000 by Anton Paar USA (League City, Tex.), was used to perform density measurements. The period of oscillation of a U-shaped borosilicate glass tube was measured for a sample ($T_1$) as well as a reference material (e.g., water or air) with known density. The relationship between the difference in density ($\rho_2 - \rho_1$) between two media and their respective oscillation periods ($T_1$ and $T_2$) is defined by the equation:

$$\rho_2 - \rho_1 = K[(T_2)^2 - (T_1)^2]$$

wherein $\rho_2$ and $\rho_1$ are the density of the surfactant and water, respectively, and k is an instrument constant determined from instrumental calibration using doubly distilled water and air. The precision of the temperature-controlled system was better than ±0.005° C.

The temperature of the sample was increased from about −160 to −110° C. to allow sublimation of any nanometer-size frost that may have condensed on the surface of the chromium film in the microscope prior to imaging. The specimens were imaged at 25 kV and digitally recorded for 30 seconds with a

TABLE 1

Physicochemical properties of the monomers and polymers of sodium N-undecenoxycarbonyl-L-amino acid sulfates (L-SUCAAS).

| CHARACTERISTIC OF THE MONOMERIC SURFACTANTS | L-SUCLS | L-SUCILS | L-SUCVS |
|---|---|---|---|
| Critical micelle concentration (CMC)[a] [mM] | 4.15 ± (0.07)* | 3.95 ± (0.36)* | 5.23 ± (0.04)* |
| Aggregation number[b] | 71 ± (1)* | 66 ± (1)* | 74 ± (1)* |
| Polarity ($I_1/I_3$) ratio[c] | 1.0246 ± (0.0004)* | 1.0844 ± (0.0014)* | 1.0413 ± (0.0002)* |
| Optical rotation[d] | −19.35 ± (0.07)* | −14.10 ± (0.14)* | −16.20 ± (0.14)* |
| Partial specific volume[e] | 0.5590 ± (0.0006)* | 0.5134 ± (0.0009)* | 0.5426 ± (0.0018)* |

| CHARACTERISTIC OF THE POLYMERIC SURFACTANTS | POLY-L-SUCLS | POLY-L-SUCILS | POLY-L-SUCVS |
|---|---|---|---|
| Aggregation number[b] | 32 ± (1)* | 42 ± (1)* | 36 ± (1)* |
| Polarity ($I_1/I_3$) ratio[c] | 1.0630 ± (0.0008)* | 1.105 ± (0.007)* | 1.076 ± (0.003)* |
| Optical rotation[d] | −22.65 ± (0.07)* | −18.10 ± (0.14)* | −19.80 ± (0.14)* |
| Partial specific volume[e] | 0.8095 ± (0.0004)* | 0.7994 ± (0.0011)* | 0.7905 ± (0.0004)* |

[a]Critical micelle concentration is determined by the surface tension measurements;
[b]Aggregation number is determined by the florescence quenching experiment using pyrene as a probe and cetyl pyridinium chloride as a quencher;
[c]Polarities of the surfactants are determined using ratio of the fluorescence intensity ($I_1/I_3$) of pyrene;
[d]Optical rotation of 1%(w/v) of monomer and micelle polymers were determined in triply deionized water; were obtained at 589 nm [sodium D line];
[e]Partial specific volumes were determined by the density measurements at different surfactant concentrations;
*Standard deviations are given in parentheses].

A comparison of the physicochemical properties of the monomeric and polymeric surfactants illustrates that the aggregation number (A) is lower, while the polarity, optical rotation, and $\overline{V}$ are higher for polymeric surfactants as compared to the corresponding monomers.

Cryogenic-High-Resolution Scanning Electron Microscopy (Cryo-HRSEM) Sample Preparation and Imaging The cryo-HRSEM was used to investigate the morphology of polymeric surfactants. Approximately 10 μL aliquots (5 mg/mL) of the polymeric sulfated surfactant (poly-L-SUCLS, poly-L-SUCILS and poly-L-SUCVS) solutions were loaded into flat-bottom-well gold planchets (Balzers BU 0120130T), plunge-frozen into liquid ethane, and stored under liquid nitrogen. The frozen samples were transferred into a pre-cooled (~−170° C.) cryo-preparation stage (Gatan CT-3500), fractured with a pre-chilled blade, and kept under liquid nitrogen. The shutters on the cryo-preparation stage were kept closed to avoid frost formation and the stage quickly was transferred into a Denton DV-602 (Moorestown, N.J.) chromium coater. Once the chromium coater was evacuated to $2\times10^{-7}$ Torr, the stage shutters were opened and the stage temperature was increased to −105° C. during the etching period. The chamber finally was refilled to $5\times10^{-3}$ Torr with argon gas.

It was determined experimentally that 6 minutes of etch time at −105° C. was needed to remove a sufficient amount of unbound water-ice, and that a concentration of 5 mg/mL of surfactant was needed to reveal any notable structural features. After etching, the temperature was returned to −170° C. and the frozen specimens were sputter-coated with 1-2 nm of chromium. The chamber of chromium coater was flushed with dry nitrogen gas (which allowed the specimen to return to atmospheric pressure) and the cold stage was removed and transferred quickly to in-lens DS-130F Field Emission SEM.

GW capture board at 17.4 Megabytes file size. Adobe Photoshop 6.0 was used to adjust levels.

The etched surface of the fractured drop of the poly-L-SUCLS revealed tubular or rod-like structures when cryo-etched for 6 minutes under low temperature-HRSEM. Nanorods having a distinct order appeared to have 80-100 nm widths, which was dependent on the amount of loosely bound water around them. The tubular structure revealed by cryo-HRSEM was reminiscent of the fact that surfactants at concentrations significantly higher than the critical micelle concentration (CMC) quickly form rod like structures while spherical micelles only exist in dilute solutions. In contrast to the morphological behavior of poly-L-SUCLS, poly-L-SUCILS displayed random distribution of coiled/curved filaments with heavy association of tightly and loosely bound water while poly-L-SUCVS showed tubular morphology without any distinct order of the tubes having widths from 120-180 nm, which was dependant on the amount of loosely bound water around them.

Example 2

Enantioseparation of Phenylethylamines

Figure 2:
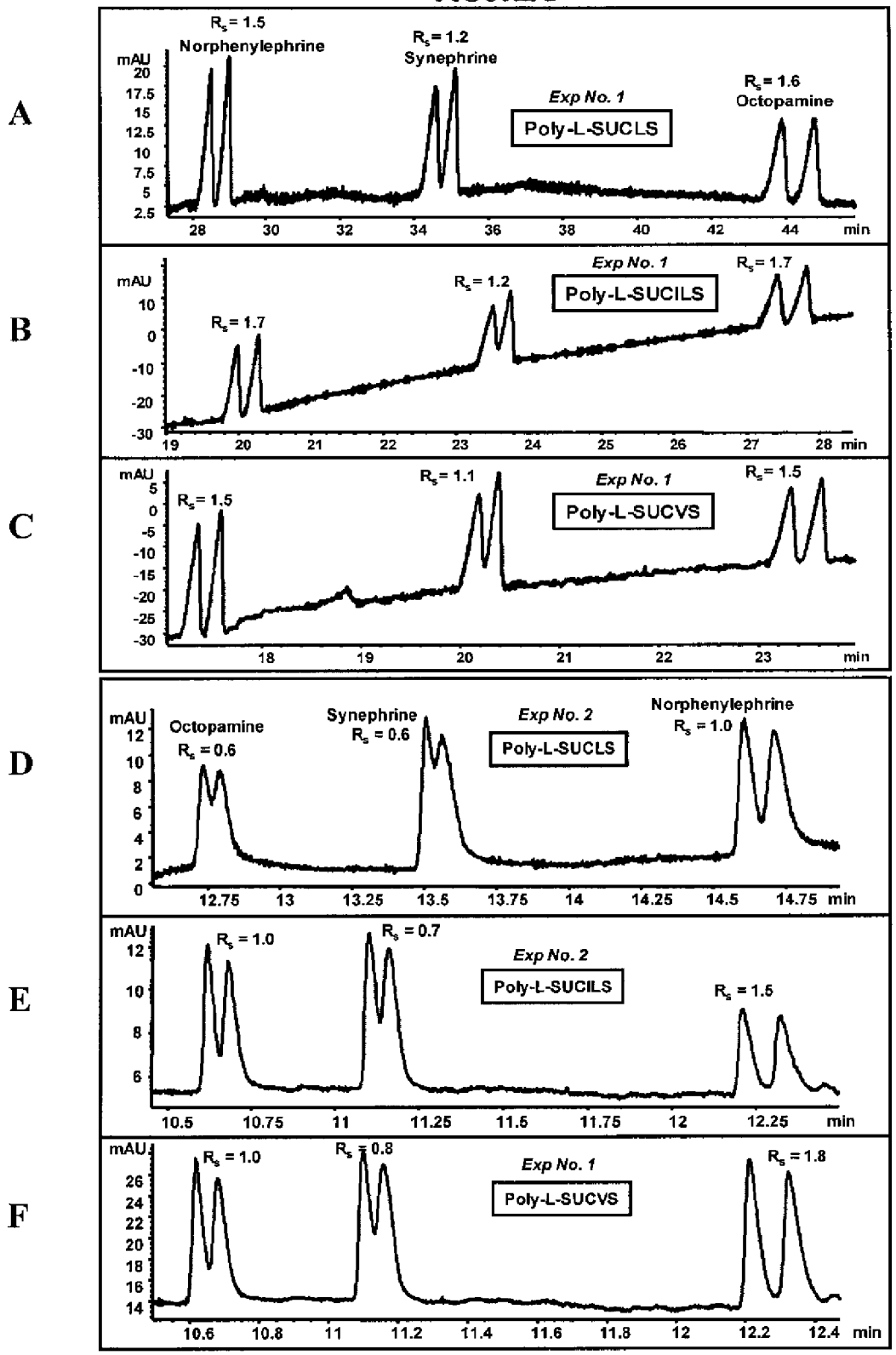
FIGS. 2A-2F illustrate chiral separation of positively charged analytes of phenylethylamines (class II) comprising one hydroxyl group at low pH and moderately acidic to neutral pH using polymeric sulfated amino acid surfactants according to particular embodiments.
Figure 3:
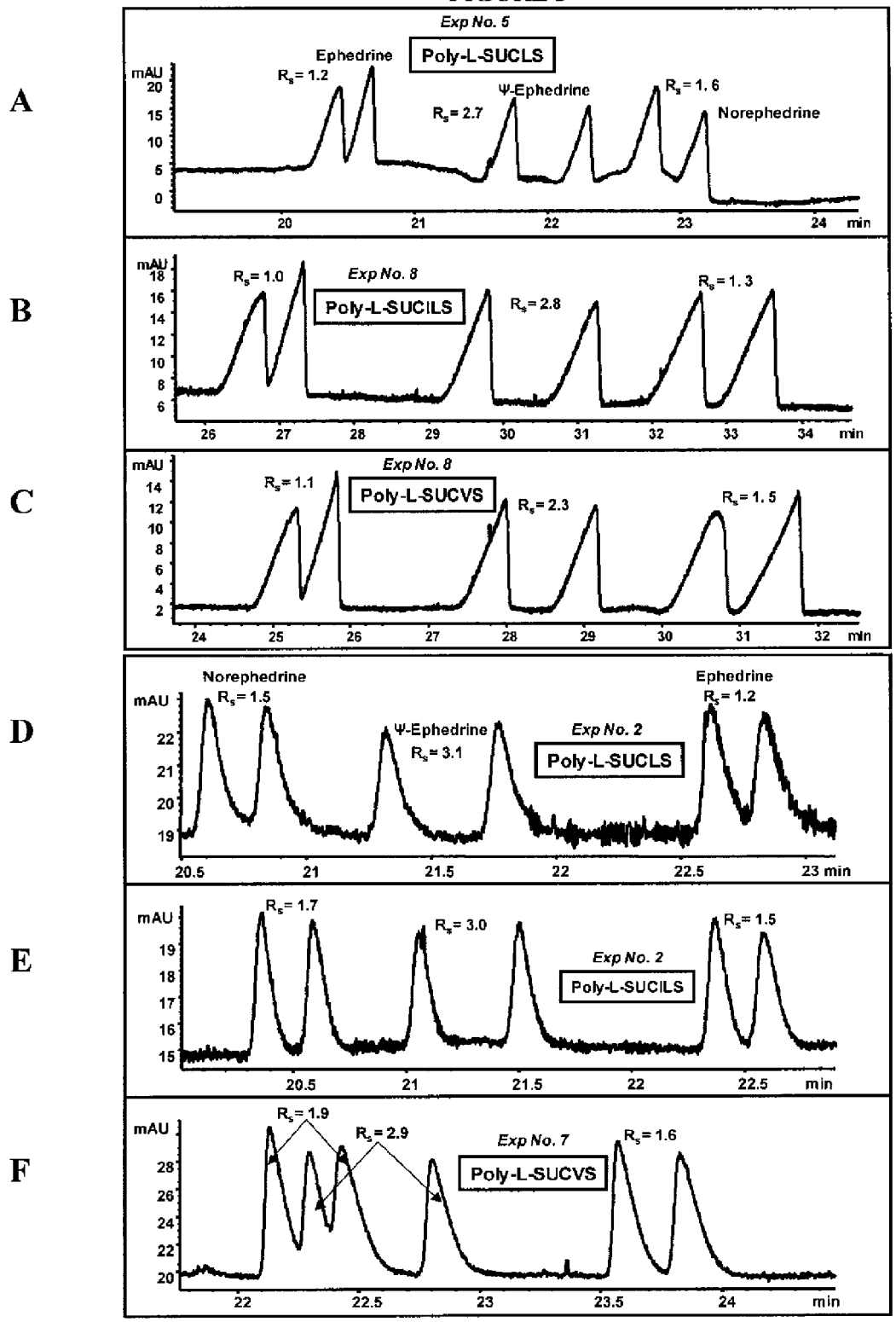
FIGS. 3A-3F illustrate chiral separation of positively charged analytes of phenylethylamines comprising no hydroxyl group (class III) at low pH and moderately acidic to neutral pH using polymeric sulfated amino acid surfactants according to particular embodiments.

The ability of the micelles embodied herein to provide chiral separation and detect positively charged analytes was measured. The positively charged analytes were selected from three classes of phenylethylamines (PEAs): one with two hydroxyl groups (FIG. 1), another with one hydroxyl group (FIG. 2), and still another with no hydroxyl groups (FIG. 3). The enantiomeric resolution was measured at both a low pH (2.0-3.0) and a high pH (6.0-7.0) using sulfated polymeric surfactants.

Identification of Factors Maximizing Chiral $R_s$ and Minimizing Analysis Time

Variables were identified which had significant effects on chiral resolution ($R_s$) and analysis time. A three-level four-factor well-balanced design from a Plackett-Burmann design (*Analy. Chim. Acta* 276, 189-95 (1993); *Electrophoresis* 26, 818-32 (2005)) was used to study the four most influential factors that maximize chiral $R_s$, and minimize analysis time (AT). The experimental designs summarized in Table 2 were executed using poly-L-SUCLS, poly-L-SUCILS and poly-L-SUCVS at an acidic pH with negative polarity and at moderately acidic to neutral pH with positive polarity. The levels (−1,0,+1) of these factors were determined using poly-L-SUCLS by running individual analytes at variable conditions of buffer concentration, pH, percentage of acetonitrile (ACN) in the buffer, temperature and surfactant concentration.

TABLE 2

Experimental design for separation strategy of PEAs using four factors at three levels under acidic pH conditions with negative polarity and moderately acidic to neutral pH with positive polarity.

| | Exp. Design Levels | | | | Exp. Design Levels | | | | | | |
|---|---|---|---|---|---|---|---|---|---|---|---|
| | | | | | (A)† | | | | (B)‡ | | |
| Exp # | pH | ACN % (V/V) | Temp/ Buffer | Micelle (mM) | pH | ACN % (V/V) | Temp (° C.) | Micelle (mM) | pH | ACN % (V/V) | Buffer⁋ (mM) | Micelle (mM) |
| 1 | −1 | 0 | 1 | 1 | 2.0 | 15 | 25 | 70 | 6.0 | 25 | 40 | 70 |
| 2 | 0 | −1 | 0 | 1 | 2.5 | 10 | 20 | 70 | 6.5 | 20 | 25 | 70 |
| 3 | 0 | 0 | −1 | 0 | 2.5 | 15 | 15 | 45 | 6.5 | 25 | 15 | 45 |
| 4 | 1 | 0 | 0 | −1 | 3.0 | 15 | 20 | 20 | 7.0 | 25 | 25 | 20 |
| 5 | −1 | 1 | 0 | 0 | 2.0 | 20 | 20 | 45 | 6.0 | 30 | 25 | 45 |
| 6 | 1 | −1 | 1 | 0 | 3.0 | 10 | 25 | 45 | 7.0 | 20 | 40 | 45 |
| 7 | 1 | 1 | −1 | 1 | 3.0 | 20 | 15 | 70 | 7.0 | 30 | 15 | 70 |
| 8 | 0 | 1 | 1 | −1 | 2.5 | 20 | 25 | 20 | 6.5 | 30 | 40 | 20 |
| 9 | −1 | −1 | −1 | −1 | 2.0 | 10 | 15 | 20 | 6.0 | 20 | 15 | 20 |

[†Low pH conditions under negative polarity;
‡Moderately acidic to neutral pH conditions;
⁋Buffer: Ammonium Acetate (NH₄OAc)].

Using negative polarity, it was found that pH (2.0-3.0), percentage of ACN [15-25% (v/v)], capillary temperature (15-25° C.) and surfactant concentrations (20-70 mM) were the four most common factors affecting $R_s$ (data not shown). Using positive polarity, the same variables were identified as being most influential with the exception of the buffer concentration, which was found to have a more significant effect on chiral $R_s$, than the capillary temperature. Other factors also were studied such as the pH range of 6.0-7.0, the ACN concentration range of 20-30% (v/v), and ammonium acetate buffer concentration range of 15-40 mM. The resolution and elution time of the second enantiomers of each analyte ($t_2$) of PEA enantiomers were chosen as response variables.

MEKC-UV and MEKC-ESI-MS Instrumentation

All chiral MEKC-UV and MEKC-ESI-MS experiments were carried out with an Agilent capillary electrophoresis instrument (Agilent Technologies, Palo Alto, Calif.) equipped with 0-30 kV high-voltage power supply, a diode array detector for UV detection, and Chemstation software (V 9.0) for system control and data acquisition. The fused-silica capillary was obtained from Polymicro Technologies (Phoenix, Ariz.). The total length of the capillary used with the Agilent CE-UV-MS system was 64.5 cm for MEKC-UV experiments (56.0 cm from inlet to detector, 50 µm ID, 350 µm OD), which was prepared by burning about 3 mm polyimide to create a detection window and 70 cm for MEKC-MS experiments. The Agilent CE system was interfaced to a single quadrupole mass spectrometer (Agilent 1100 series MSD) using a G1603A CE-MS adapter kit and a G1607 CE-ESI-MS sprayer kit (all from Agilent Technologies). An Agilent 1100 series HPLC pump equipped with a 1:100 splitter was used to deliver the sheath liquid. The Agilent Chemstation and CE-MS add-on software were used for instrument control and data analysis.

Capillary Electrophoresis Procedures

The capillaries for all MEKC experiments were prepared by flushing the capillaries with 1 N aqueous $NH_3$ for 1 hr at 50° C., rinsing the capillaries for 30 minutes with triply deionized water at a temperature desired for chiral separation, flushing the capillaries for 2 minutes with buffer, and finally running an MEKC buffer containing surfactant through the capillaries for 7 minutes. In addition, the capillary was flushed for 3 minutes with both a 0.1 N aqueous $NH_3$ and $H_2O$ and finally equilibrated with a running buffer for 7 minutes between the runs. All separations were performed at ±20 kV and at 20° C. unless otherwise mentioned. All classes of analytes were evaluated for enantioseparation using a new capillary (cut to the same length from the same capillary bundle that was preconditioned as described above).

Enantioseparation of Class I Phenylethylamines

Four analytes of class I PEAs were used to test the chiral separation ability of the micelles embodied herein. All four analytes of class I PEAs shared two common features, possessing both two phenolic hydroxy groups as well as a chiral center bearing β-amino alcohol functionality. In particular, two of the class I PEAs [(±)-epinephrine and (±)-norepinephrine] are neurotransmitters, while the other two [(±)-terbutaline and (±)-isoproterenol] are adernergeric receptor blockers.

The best polymeric sulfated surfactants were determined with a test mixture of the four class I PEAs. The poly-L-SUCILS showed the highest enantioresolution for (±)-isoproterenol ($R_s$ 2.2, Exp 8), followed by poly-L-SUCLS, where (±)-terbutaline was separated best ($R_s$=1.5, Exp 5) (data not shown). Moreover, poly-L-SUCVS provided the highest chiral resolution values ($R_s$=0.9 and 1.2, Exp 3) for (±)-epinephrine and (±)-norepinephrine, respectively (data not shown). FIGS. 1A, B, and C (pH 2.0-3.0 range) and 1D, E, and F (pH 6.0-7.0 range) show representative electropherograms of class I PEAs under the most suitable separation conditions that resulted in simultaneous enantioresolution of all four class I PEAs. The enantiomeric migration order (e.g., (±)-terbutaline and (±)-isoproterenol) not only was reversed, but also was eluted with opposite migration order for all four PEAs. Individually, however, all class I PEAs provided optimum $R_s$, at different experimental design conditions, behaving differently in terms of chiral separation under identical experimental conditions.

At low pH conditions (pH 2.0-3.0), poly-L-SUCLS (FIG. 1A) provided simultaneous enantioseparation of all four class I PEAs with the shortest analysis time under experimental condition number 6, while simultaneous enantioseparation was optimum for poly-L-SUCILS (FIG. 1B) and poly-L-SUCVS (FIG. 1C) under experimental condition number 1. In general, moderate to higher polymeric surfactant concentrations (e.g., 45 mM and 70 mM) resulted in enantioseparation of all four class I PEAs for most of the experimental conditions (data not shown); however, at relatively lower surfactant concentrations either no enantioresolutions [e.g., $R_s$=0 for (±)-epinephrine and (±)-norepinephrine] or much lower enantioresolutions [e.g., (±)-terbutaline and (±)-isoproterenol] were observed (data not shown). In addition, the migration times were substantially higher at the lowest concentration of poly-L-SUCAAS, suggesting that higher surfactant concentrations use the carrier capability of poly-L-SUCAAS as a driving force not only for faster elution, but also for higher enantioseparation.

In contrast to acidic pH conditions, the moderately acidic to neutral pH range (6.0-7.0) produced barely any resolution for (±)-isoproterenol and (±)-terbutaline, and (±)-norepinephrine and (±)-epinephrine were never separated into enantiomers. For example, poly-L-SUCLS (FIG. 1D) partially resolved terbutaline under only one experimental condition, whereas simultaneous enantioseparation of (±)-isoproterenol and (±)-terbutaline only was achieved using poly-L-SUCILS (FIG. 1E) and poly-L-SUCVS (FIG. 1F) under experimental conditions 5 and 7, respectively. Nevertheless, the class I PEAs provided significantly higher enantioselectivity using the three polymeric sulfated surfactants at low pH conditions.

Not wishing to be bound by any theory, the higher $R_s$, obtained at lower pHs could be the result of the conformational transition of poly-L-SUCAAS from a more compact structure at a low pH (2.0-3.0) to a less compact structure at a moderately acidic to neutral pH (6.0) as depicted by the $I_I/I_{III}$, ratio of the pyrene emission spectrum. For example, it was observed that for poly-L-SUCVS the polarity first slowly decreased (1.195 to 1.182) with an increased pH (2.0 to 4.0), and then increased (1.182 to 1.236) with a further increase in pH (4.0 to 6.0), and finally remained fairly constant (1.236 to 1.238) with still a further increase in pH (6.0 to 8.0) (data not shown). Similar polarity trends also were observed for poly-L-SUCLS and poly-L-SUCILS. This pH-dependent conformational transition of polymeric surfactant also has been reported by Chu and Thomas (*Mucromolecules* 24, 2133-38 and 22212-16 (1991), while Wang and Warner (*Anal. Chem.* 66, 3773-76 (1994)) observed an opposite trend using an amide based polymeric surfactant polysodium N-undecenyl-L-valinate, in which enhanced chiral separation of (+)-laudanosine enantiomers was observed at a pH of 10.0 as compared to a pH of 8.5. The results obtained in the experiments provided herein appear to indicate that at lower pHs the compact conformation of the polymeric sulfated surfactants favored the chiral interactions with the positively charged class I PEAs. In addition, separation under acidic conditions not only resulted in very low electroosmotic flow (EOF), but also increased the effective positive charge on the PEAs, thereby leading to enhanced chiral recognition.

Enantioseparation of Class II Phenylethylamines

The Class II PEAs used to test the chiral separation of the micelles embodied herein include three biologically active compounds bearing one hydroxy group on the benzene ring: (±)-synpehrine, (±)-octopamine, and (±)-norphenylephrine. Similar to the enantioseparation of the class I PEAs, all class II PEAs showed a maximum chiral $R_s$, at different experimental conditions. For example, poly-L-SUCLS provided the highest enantiomeric resolution for (±)-synephrine ($R_s$=2.0), (±)-octopamine ($R_s$=2.1), and (±)-nor-phenyephrine ($R_s$=2.6), under experimental conditions 4, 5 and 8, respectively, but at the expense of longer AT (data not shown). However, longer AT also was observed with poly-L-SUCVS when the $R_s$ factor was maximized. In contrast, poly-L-SUCILS gave baseline $R_s$ for the three class II PEAs without excessive AT.

The overall quality of simultaneous enantioseparation was assessed based on $R_s \geq 1$ for (±)-synephrine and (±)-octopamine; and $R_s > 1.5$ for (±)-norphenylephrine with the least possible AT. The class II PEAs at low pH showed optimum simultaneous separation under the same experimental condition (1) irrespective of the type of polymeric surfactant (FIGS. 2A, B, C). Similar to the chiral separation of the class I PEAs at low pH, the class II PEAs provided the best $R_s$ at higher surfactant concentrations (45-70 mM) as compared to lower surfactant concentrations (20 mM), where either no $R_s$ or very low $R_s$ were observed, mainly due to very long AT.

Under moderately acidic to neutral pH, poly-L-SUCLS (FIG. 2D) and poly-L-SUCILS (FIG. 2E) provided optimal simultaneous enantioseparation under experimental condition 2 while poly-L-SUCVS (FIG. 2F) provided optimal simultaneous enantioseparation under experimental condition 1. FIGS. 2A, B, and C show representative electropherograms for an acidic pH of 2.0, which resulted in overall chiral $R_s \geq 1$ of all three class II PEAs using poly-L-SUCAAS. Similar to the results obtained for the class I PEAs, the elution order of the class II PEAs was reversed in the pH range of 6.0-7.0 (FIGS. 2D, E, F) and all three stereoisomers of the class II PEAs had better resolution for a low pH of 2.0 as compared to a moderately acidic pH of 6.0 or 6.5.

Enantioseparation of Class III Phenylethylamines.

The Class III PEAs used to test the chiral separation of the micelles embodied herein commonly are known as the ephedra alkaloids and include the stereoisomers of (±)-ephedrine, (±)-pseudoephedrine, and (±)-norephedrine. These compounds have been used to treat symptoms of cold and cough, reduce fever and induce perspiration. (*Biomed. Chromatogr.* 19, 337-42 (2005)). In general, the enantiomers of this class of PEAs had the best resolution using either poly-L-SUCLS (FIG. 3A) or poly-L-SUCILS (FIG. 3B) at acidic pH, whereas at moderately acidic to neutral pH conditions poly-L-SUCILS (FIG. 3E) and poly-L-SUCVS (FIG. 3F) seemed to provide the maximum $R_s$. Furthermore, unlike several compounds of class I and class II PEAs, where chiral $R_s$ was essentially zero at lower polymeric surfactant concentrations, the class III PEAs provided chiral resolution even at lower concentrations of polymeric sulfated surfactants. In fact, under all experimental conditions (irrespective of pH and polarity of power supply) some level of chiral $R_s$ was observed for every compound of the class III PEAs (data not shown).

FIG. 3 shows the enantioseparation of class III analytes under very acidic (FIGS. 3A, B, C) and moderately acidic to neutral pH conditions (FIGS. 3D, E, F). Similar to the separation of class I and II PEAs, the elution order of class III PEAs was found to be reversed in the pH range of 2.0-3.0 (FIGS. 3A, B, C) as compared to pH range of 6.0-7.0 (FIGS.

3D, E, F). At low pHs the peaks tended to front while at moderately acidic to neutral pHs the peaks tended to tail. Not wishing to be bound by any theory, such a trend may be due to the mobility mismatch between the analyte and the background electrolyte ions.

When comparing the chiral $R_s$ among class I, II and III PEAs, the Rs was enhanced dramatically with decreasing substitution of phenolic hydroxy group on the benzene ring, providing the following order of chiral $R_s$: class I (two hydroxy groups)>class II (one hydroxy group)>class III (no hydroxy group). Not wishing to be bound by any theory, such a trend may be due to the phenolic hydroxy groups on the benzene ring of PEA competing with a hydroxy group located adjacent to the chiral center for the hydrogen bonding interactions with the highly functionalized chiral polymeric sulfated surfactants.

Example 3

Application of Optimized MEKC-MS Conditions for Sensitive Pseudoephedrine Assay in Human Urine Sample The applicability of the chiral polymeric sulfated surfactants provided herein were used in a quantitative chiral assay for one of the PEAs [e.g., (±)-pseudoephedrine] found in human body fluid. The enantiomer (1S,2S)-(+)-pseudoephedrine is the most commonly used over-the-counter cough medicine and often has been misused for its stimulant properties. (±)-pseudoephedrine also has been used as a precursor for the clandestine production of methamphetamine and related illicit drugs. The serum half-life of (±)-pseudoephedrine is 5-8 hrs and about one-half of the dosage taken is excreted in the urine.

Figure 4A:
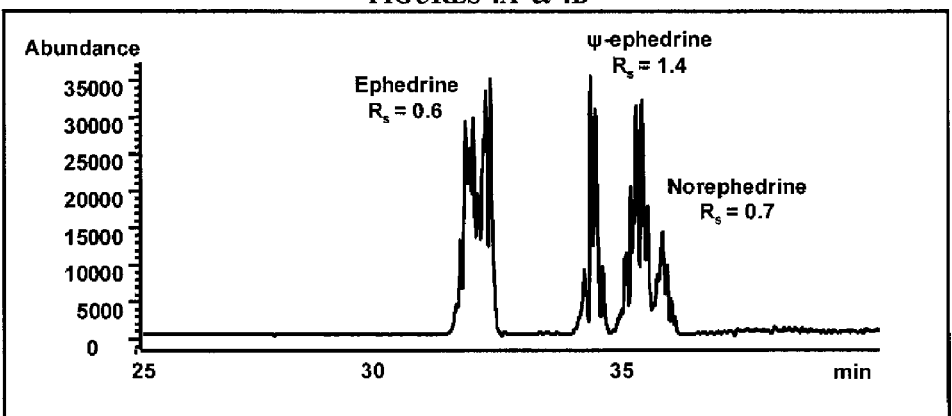
FIGS. 4A & 4B illustrate the chiral separation of positively charged analytes of phenylethylamines comprising no hydroxyl group (class III) using polymeric sulfated amino acid surfactants according to a particular embodiment both without and with valeric acid in the sheath liquid, respectively.
Figure 4B:
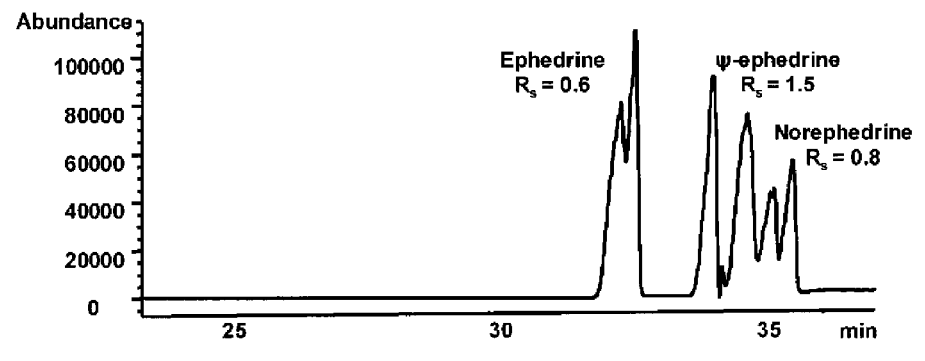

Poly-L-SUCLS was used for the identification of the presence of (±)-pseudoephedrine in human urine and the limit of detection (LOD) was compared for both low and high pHs. A chiral MEKC-MS method development was performed on class III PEAs to obtain optimum sheath liquid and MS spray chamber parameters (data not shown). FIGS. 4A and 4B show a comparison of MEKC-MS of class III PEAs under optimum conditions. When ammonium acetate was used in the sheath liquid, severe arcing was observed even though a polymeric surfactant was employed (FIG. 4A). Not wishing to be bound by any theory, this observation may be due to the fact that the class III PEAs are positively charged and form very strong ion pairs at low pHs with the negatively charged poly-L-SUCLS. Thus, the tightly bound ion-pairs have difficulty escaping from the electrospray droplet, reducing sensitivity. To overcome this problem, a volatile acidic ion pairing reagent (e.g., valeric acid) which competes for the ion-pair formation with the positively charged analyte was used, resulting in an almost 3-fold higher sensitivity with almost no arcing and background noise (FIG. 4B).

Figures 5A, 5B:
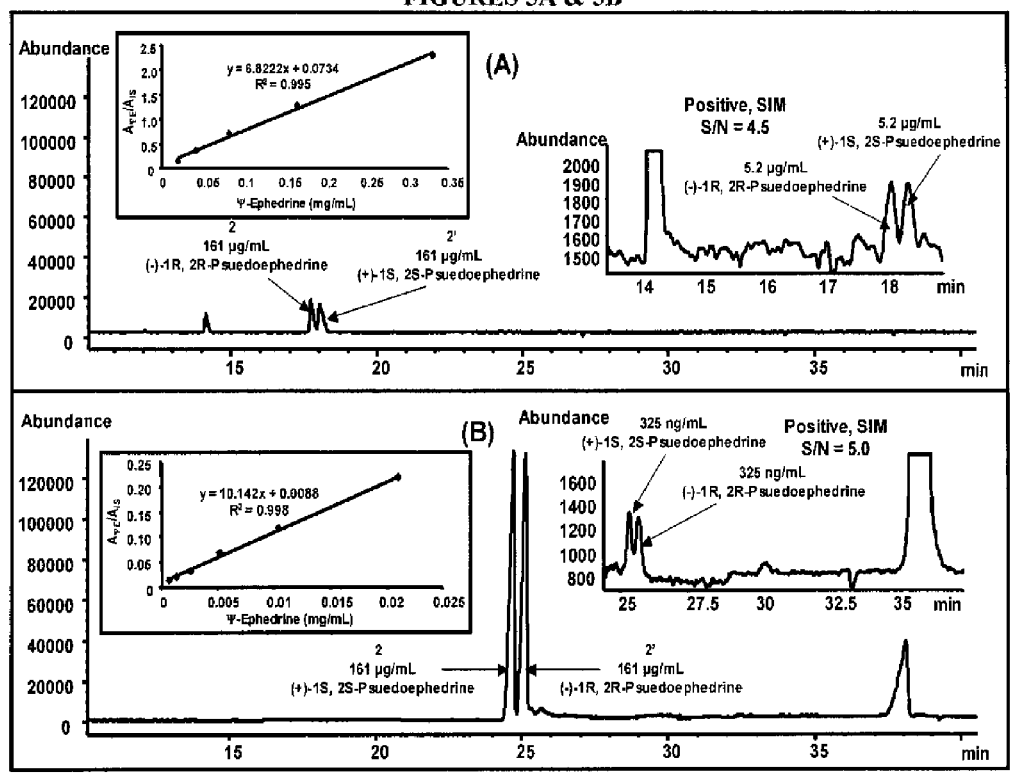
FIGS. 5A & 5B illustrate an analysis of human urine spiked with pseudoephedrine enantiomers in MEKC-MS at low and high pHs, respectively, using polymeric sulfated amino acid surfactants according to a particular embodiment. The insets on the right and left of each figure show the enhanced region for pseudoephedrine at the LOD and calibration curves for pseudoephedrine enantiomers, respectively.

The electropherograms of FIGS. 5A and 5B illustrates that under similar MEKC-MS conditions, with the exception of the BGE pH, the signal intensity obtained at low a pH (FIG. 5A) was approximately 6-fold higher as compared to at a high pH (FIG. 5B). Consequently, approximately 16 times lower LOD (i.e., 325 ng/mL) can be achieved at low pH (pH 2.0) as compared to the LOD (5.2 µg/mL) obtained at high pH (pH 8.0). Not wishing to be bound by any theory, this very low LOD may be related to the fact that at a low pH of 2.0 and negative polarity configuration with zero electroosmotic flow, poly-L-SUCLS migrated towards the MS detector and its carrier capability was used as a driving force for elution of (±)-pseudoephedrine. This carrier capability of poly-L-SU-CLS may be attributed to the electrostatic attraction between the negatively charged micelle and the positively charged analyte. Thus, the majority of the analyte molecules migrated to the MS detection in the complexed form with the chiral micelle providing enhanced detection. At low pHs, preconcentration also might result from the combined effect of sweeping and the field-amplified sample stacking (*J. Sep. Sci* 25, 215-21 (2002)). Conversely, at pHs of 8.0 and normal polarity configuration, the self-mobility of a chiral micelle is away from the MS detector and will result in fewer analyte molecules entering into the MS detector as compared to that at a pH 2.0.

Example 4

Enantioseparation of β-Blockers

Figure 6:
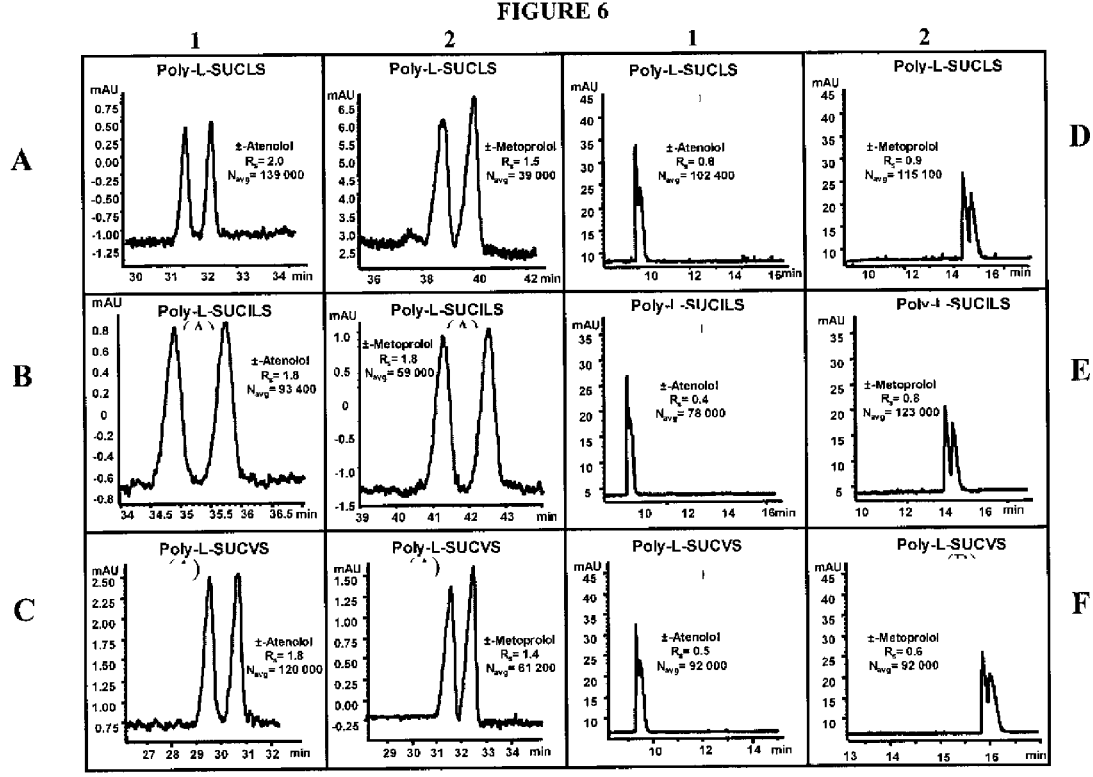
FIGS. 6A-6F illustrate the chiral separation of the β-blockers (±)-atenolol and (±)-metoprolol using polymeric sulfated amino acid surfactants according to particular embodiments.

FIG. 6 shows comparisons of the enantioseparation of two β-blockers, (±)-atenolol (FIGS. 6 A1-F1) and (±)-metoprolol (FIGS. 6 A2-F2), at low (FIGS. 6 A1-A2, B1-B2, C1-C2) and high pHs (FIGS. 6 D1-D2, E1-E2, F1-F2) under optimum conditions of poly-L-SUCLS (FIGS. 6 A1-A2, D1-D2), poly-L-SUCILS (FIGS. 6 B1-B2, E1-E2) and poly-L-SUCVS (FIGS. 6 C1-C2, F1-F2). The electrokinetic chromatograms show that at a low pH (FIGS. 6 A1-A2, B1-B2, C1-C2), (±)-atenolol and (±)-metoprolol required longer AT and always achieved the baseline resolution, while at a high pH (FIGS. 6 D1-D2, E1-E2, F1-F2) only partial separation was obtained. Not wishing to be bound by any theory, it is believed that the improved chiral resolution of the two β-blockers using any of the three polymeric surfactants at a low pH may be attributed to the change in conformation of the polymeric sulfated surfactant associated with the pH variations. It was observed that at a low pH, hydrophilic β-blocker (±)-atenolol required higher polymeric surfactant concentrations (i.e., 35 mM) than the moderately hydrophobic analyte, (±)-metoprolol, which required lower polymeric surfactant concentrations (i.e., 15 mM) for chiral $R_s$ in accordance with the hydrophobicity of the analyte. It also was observed that increasing the polymeric surfactant concentration decreased the retention time of β-blockers at a low pH of 2.0 when using negative polarity, whereas the opposite was found to be true at a high pH of 8.0 when using positive polarity (data not shown).

Example 5

Enantioseparation of ±-2-(2-chlorophenoxy)propanoic Acid

Figure 7:
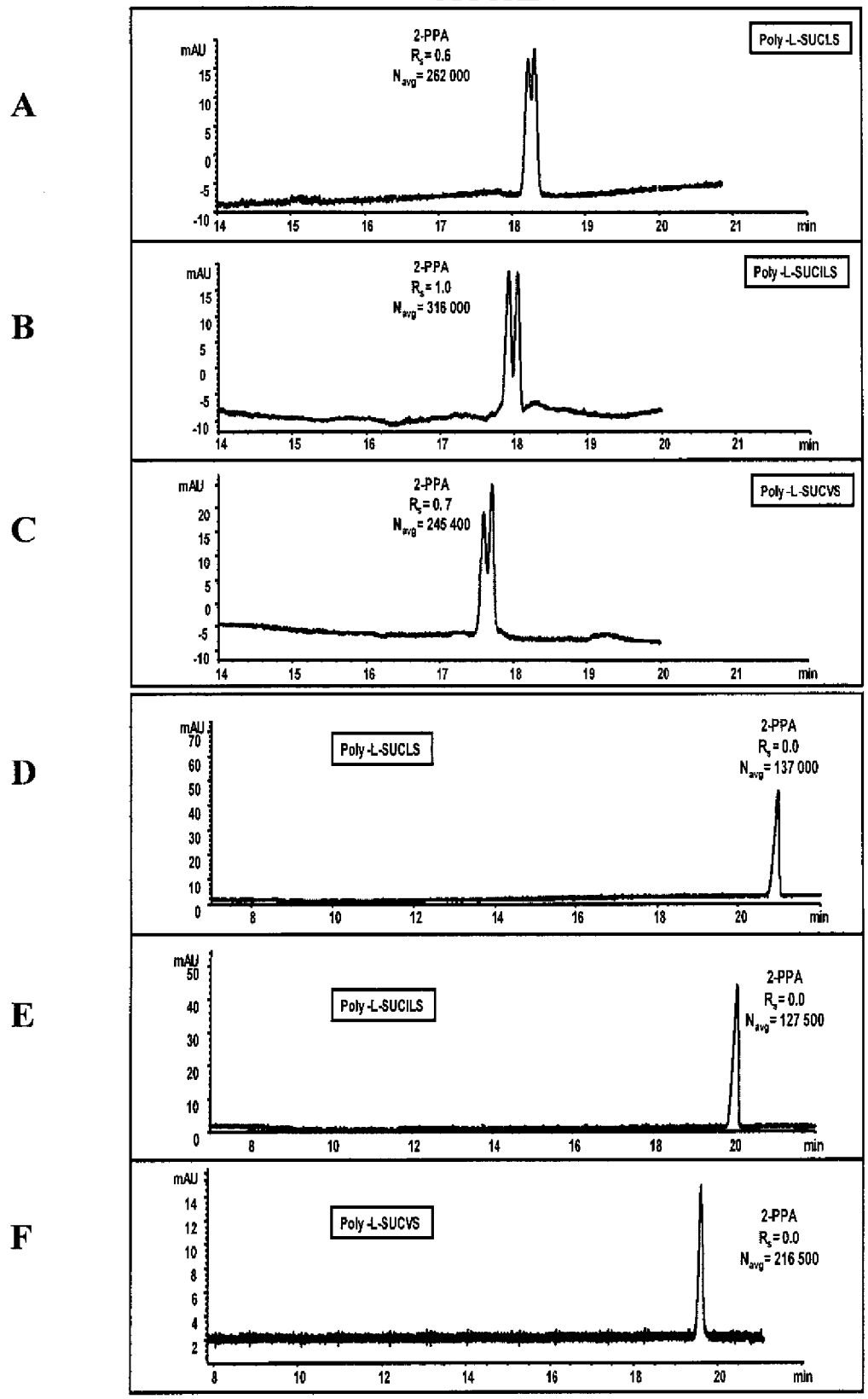
FIGS. 7A-7F illustrate the chiral separation of anionic racemic compound 2-(2-chlorophenoxy)propionic acid (2-PPA) using polymeric sulfated amino acid surfactants according to a particular embodiment at both a low pH and a high pH.

The enantiomers of (±)-2-PPA exist predominantly in the anionic form at pH≧3.0 (pKa=3.11±0.1). This anionic chiral compound has been used for synthesis of antibiotics and often used as a herbicide. The chiral separation of (±)-2-PPA with all three poly-L-SUCAAS was compared at both low (FIGS. 7A, B, C) and high pHs (FIGS. 7D, E, F). The enantiomers of (±)-2-PPA, because of inherent negative charge, poorly interact due to electrostatic repulsion with chiral anionic polymeric sulfated surfactants at basic pH. Therefore, as expected, no chiral resolution was obtained for (±)-2-PPA at pH 8.0. Since poly-L-SUCAAS has a sulfated head group and is readily soluble in very low pH buffer, chiral separation was attempted at pH 2.0 (FIGS. 7A, B, C) where (±)-2-PPA is essentially neutral (pKa 3.11±0.10). It can be seen in FIGS. 7A, B, and C that partial chiral $R_s$ of (±)-2-PPA was achieved at pH 2.0 with any of the three poly-L-SUCAAS surfactants. The successful enantioseparation of negatively charged (±)-2-PPA obtained with anionic poly-L-SUCAAS at low pH confirms that electrostatic attractive interactions significantly contributes in the binding of charged analytes with oppositely charged polymeric surfactant. However, these interactions are not always the only major factor for chiral recognition. The hydrogen-bonding capability of the ether and the carboxylate groups in (±)-2-PPA also are important in chiral discrimination using poly-L-SUCAAS surfactants. It is apparent from the electropherograms that poly-L-SUCILS (FIG. 7B) possessing two chiral centers provided slightly enhanced chiral $R_s$ and N compared to poly-L-SUCLS (FIG. 7A) and poly-L-SUCVS (FIG. 7C) with one chiral center. However the chiral $R_s$ of (±)-2-PPA could not be improved any further even after fine-tuning of the MEKC parameters (data not shown).

Example 6

Enantioseparation of (±)-Benzoin Derivatives

Figure 8:
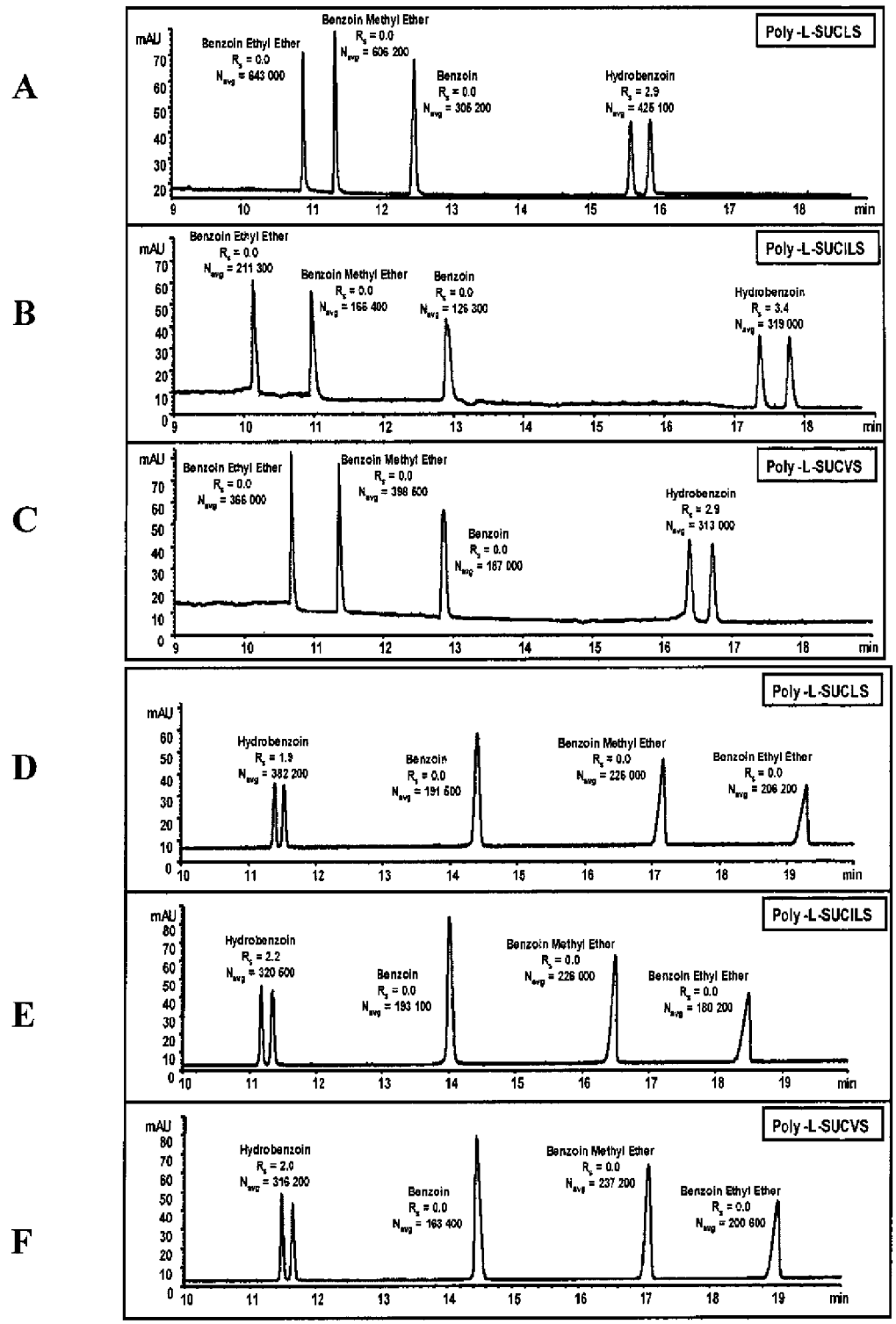
FIGS. 8A-8F illustrate the chiral separation of four benzoin derivatives using polymeric sulfated amino acid surfactants according to particular embodiments at both a low pH and a high pH.

FIG. 8 shows the simultaneous separation of four structurally related benzoin derivatives using all three poly-L-SUCAAS at two different pHs and with opposite polarity of high voltage power supply. The chiral separation of benzoin derivatives was performed to evaluate the effects of steric, hydrophobic and hydrogen-bonding factors on the enantioselective interactions among these analytes and poly-L-SUCAAS. As shown in FIGS. 5A, B, and C, the most hydrophobic benzoin derivative (e.g., benzoin ethylether) eluted first, whereas the most hydrophilic benzoin derivative (e.g., (±)-hydrobenzoin) eluted last at low pH conditions under zero EOF and negative polarity of the voltage supply. Conversely, at high pH conditions the elution order of benzoin derivatives was reversed (FIGS. 7D, E, F). Under both high and low pH conditions, only (±)-hydrobenzoin could be separated into enantiomers; however, higher resolution always was obtained at low pHs irrespective of the type of the polymeric sulfated surfactant. Not wishing to be bound by any theory, it appears that the structural rigidity of (±)-benzoin, (±)-benzoin methylether, and (±)-benzoin ethylether due to the presence of carbonyl group completely hampers the enantioselective interactions between these analytes and poly-L-SUCAAS. Accordingly, the significant difference in chiral recognition is believed to be due to the additional hydroxy group and lower rigidity of (±)-hydrobenzoin as compared to the other benzoin derivatives. Among poly-L-SUCAAS, the two chiral center-bearing poly-L-SUCILS (FIGS. 8B, E) exhibited slightly higher enantioseparation of (±)-hydrobenzoin at both low and high pHs.

Example 7

Enantioseparation of (±)-PTH-amino Acids

Figure 9:
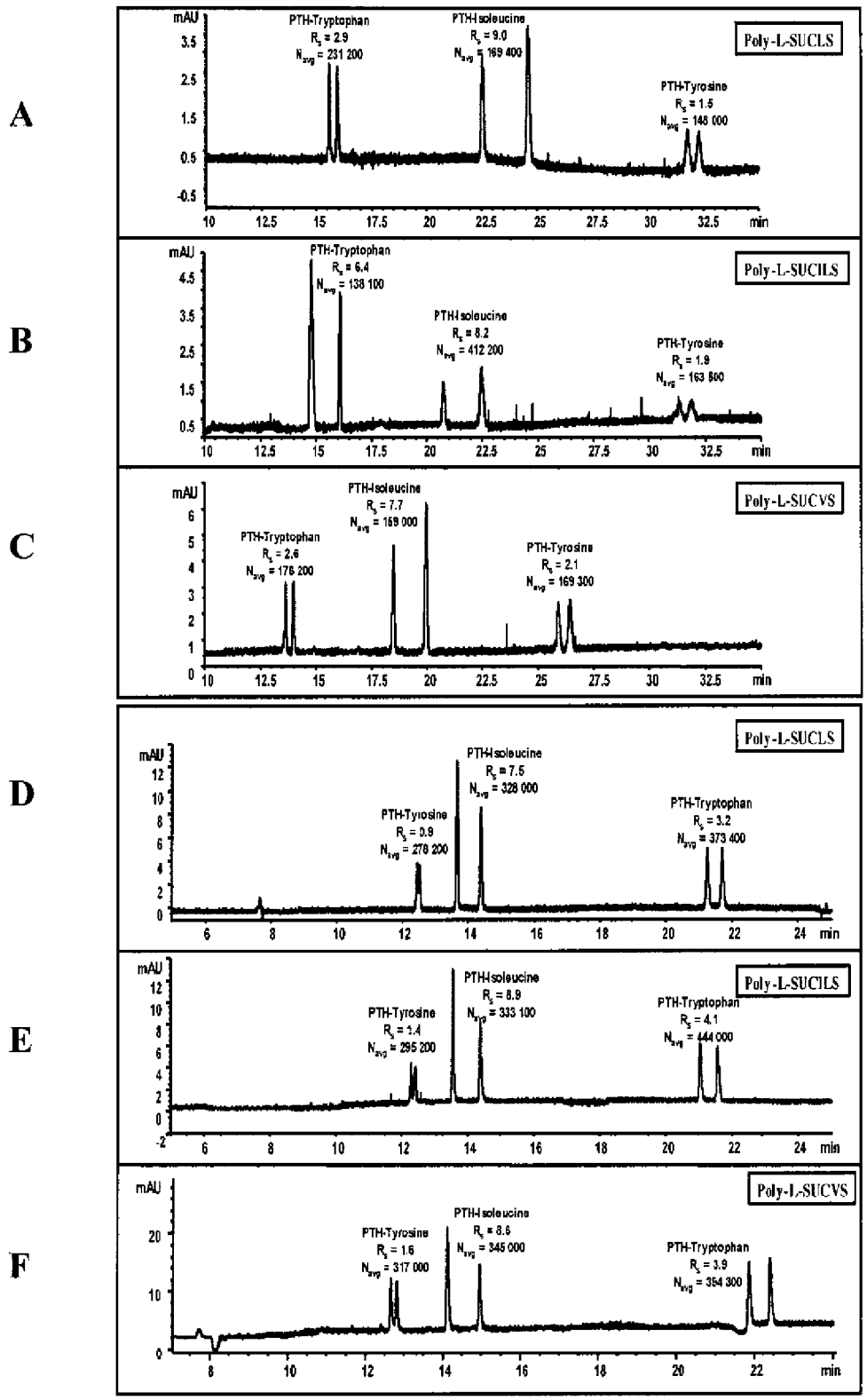
FIGS. 9A-9F illustrate the chiral separation of neutral analytes of phenylthiohydantoin (PTH) derivatives of amino acids using polymeric sulfated amino acid surfactants according to a particular embodiment at both a low pH and a high pH.

FIG. 9 shows the chiral separation of three PTH-amino acids (AAs): (±)-PTH-tyrosine, (±)-PTH-isoleucine and (±)-PTH-tryptophan. The migration order of all three PTH AAs and their respective enantiomers was opposite under low (FIGS. 9A, B, C) and high (FIGS. 9D, E, F) pH conditions. At low pHs (FIGS. 9A, B, C), using any of the three polymeric surfactants, baseline resolution values were obtained for (±)-PTH-tyrosine and compared to the partial resolution observed at high pHs with two of the polymeric surfactants (FIGS. 9D, E, F). The aromatic side chain containing PTH-amino acids (e.g., (±)-PTH-tyrosine and (±)-PTH-tryptophan) both showed inferior enantioselectivity with any of the three poly-L-SUCAAS compared to non-aromatic side chain containing PTH-amino acid (e.g., (±)-PTH-isoleucine).

Similar to results obtained with (±)-2-PPA, (±)-atenolol and (±)-hydrobenzoin, at both low and high pHs poly-L-SUCILS (FIGS. 9B, E) provided the highest chiral resolution when compared to poly-L-SUCLS (FIGS. 9A, D)) and poly-L-SUCVS (FIGS. 9C, F). Not wishing to be bound by any theory, this improved chiral separation capability of poly-L-SUCILS may be due to the presence of two chiral centers in poly-L-SUCILS, one of which is located near the surface of the micelle (on the side chain of the amino acid), easing the chiral interaction between the analyte and polymeric surfactant.

Example 8

Enantioseparation of (±)-Benzodiazepines

Figure 10:
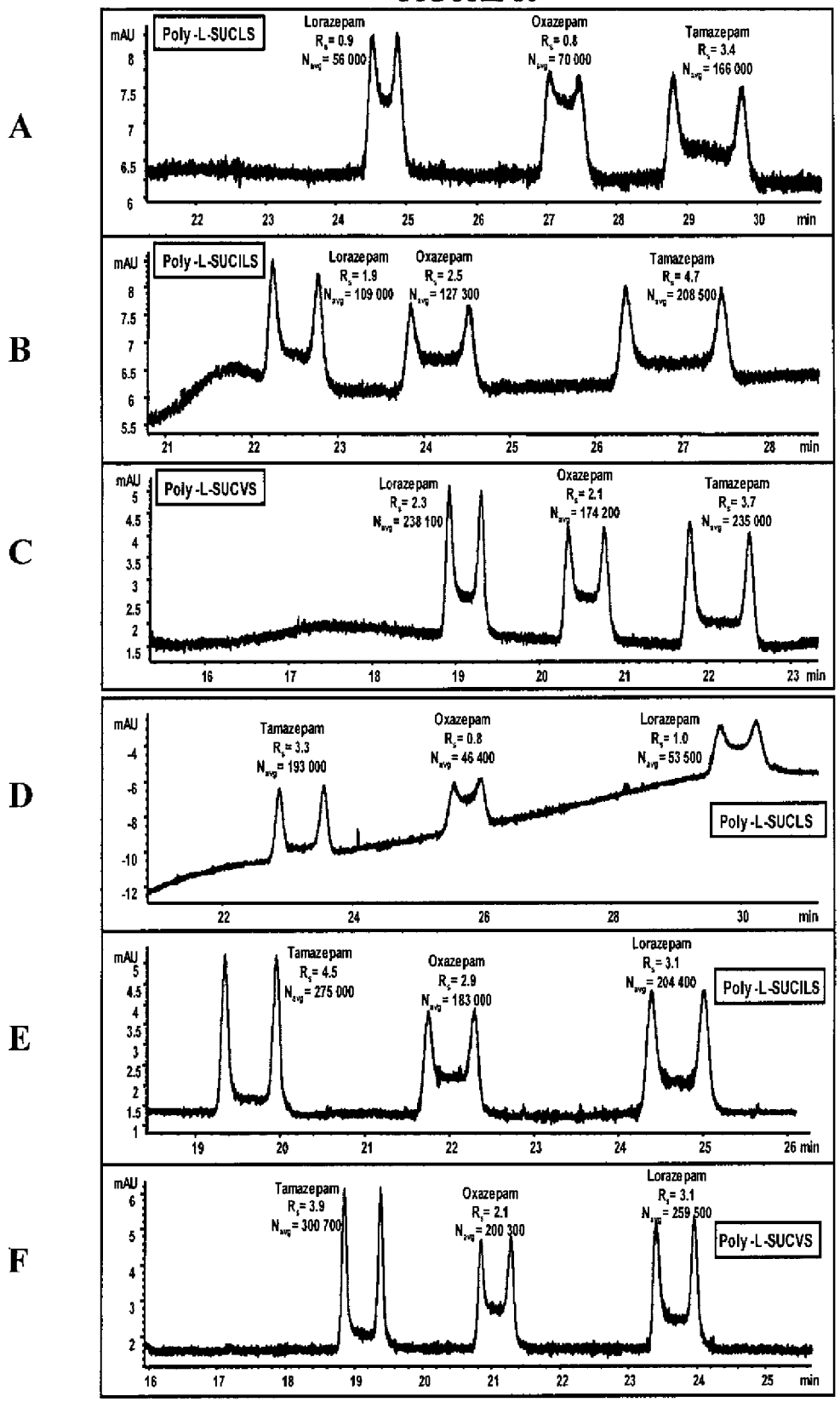
FIGS. 10A-10F illustrate the chiral separation of benzodiazepines using polymeric sulfated amino acid surfactants according to a particular embodiment at both a low pH and a high pH.

Three chiral and structurally related benzodiazepines also were separated at both low and high pH conditions employing poly-L-SUCLS, poly-L-SUCILS, and poly-L-SUCVS (FIG. 10). All three chiral benzodiazepinones showed enantiomerization during chiral separation. The process of enantiomerization previously has been reported in GC, HPLC, and CE for the chiral separation of benzodiazepinones and often results in plateau formation and ultimately peak coalescence. The three chiral benzodiazepinones studied have similar molecular structures, differing only by the presence of chloro group on the phenyl ring and methyl group at the amide nitrogen in the benzodiazepinone skeleton. The migration order of the separated benzodiazepinones was reversed at low (Figures A, B, C) and high (Figures D, E, F) pHs. At both low pHs and high pHs, (±)-temazepam provided the highest resolution (irrespective of its elution order), followed by (±)-lorazepam and (±)-oxazepam for all three polymeric sulfated surfactants. Not wishing to be bound by any theory, it appears that the introduction of methyl group at the amide nitrogen in the benzodiazepinone skeleton enhanced the chiral interaction between the (±)-temazepam and the poly-L-SACAAS. It is believed this eliminated the competition for hydrogen bonding interactions between the amide proton and hydroxyl proton (located next to the chiral center) on the analyte.

Akbay et al. tested the applicability of copolymerized surfactants obtained by polymerizing a chiral surfactant (sodium 10 undecenoyl-L-leucinate) with various molar fractions of achiral monomeric surfactant (sodium 10 undecenyl sulfate) for the enantioseparation of three benzodiazepines. (*Electrophoresis* 24, 4209-20 (2003)). The enantiomers of (±)-temazepam provided the highest the resolution as value compared to the other two benzodiazepines [(±)-oxazepam and (±)-lorazepam] at pH 8.0. However, the chiral resolution was found to decrease as the mole fraction of achiral sulfated surfactant increased in the co-polymer. Of the polymeric sulfated surfactants described herein, the two chiral center bearing poly-L-SUCILS (FIGS. 10B, E) provided better chiral resolution of benzodiazepinones as compared to single chiral center poly-L-SUCLS (FIGS. 10A, D) and poly-L-SUCVS (FIGS. 10C, F).

The results described hereinabove demonstrate successful chiral separations of a large number of structurally diverse acidic, basic, and neutral racemic compounds when compared both at low and high pH conditions in MEKC using polymeric sulfated surfactants.

Example 9

Enantioseparation By Open-Tubular Capillary Electrochromatography

The separation of chiral mixtures also may be conducted using open-tubular capillary electrochromatography (OT- CEC). A polyelectrolyte multilayer (PEM) coating on the inside walls of a capillary may be constructed by flushing cationic and anionic polymer deposition solutions through the capillaries, with at least the last (or innermost) anionic polymer layer comprising the sulfated polymeric micelles embodied herein. The alternating layers of positively and negatively charged polymers are created by electrostatic forces, such that one layer of polymer adds to the existing oppositely-charged surface, thereby reversing the surface charge and priming the film for the addition of another layer. The cationic and anionic polymer solutions generally are deposited in the presence of a salt, such as sodium chloride, and also may contain the salt. The polymeric layers also may comprise modifiers, such as an organic solvent, and may comprise other weak polyelectrolytes. Those of ordinary skill in the art will appreciate that the PEM may comprise any number of layers, desirably with the innermost layer comprising the anionic polymer comprised by the sulfated polymeric micelles embodied herein.

Suitable cationic polymers should have a sufficient charge density to form stable multilayers via electrostatic interactions, such that the charge density may vary as a function of hydrophobicity. Such cationic polymers are well known to those of ordinary skill in the art, non-limiting examples of which include polyelectrolytes with a quaternary ammonium group, ionenes, cationic polyacrylamides, polyelectrolytes with a pyridinium group, protonated polyamides, polyethyleneimine, polybrene, and their corresponding copolymers.

Those of ordinary skill in the art will appreciate that the internal diameter of the fused silica capillary generally will be between about 1 and about 500 µm, more desirably between about 5 and about 200 µm, and still more desirably between about 50 and about 75 µm. Such capillaries may be formed using any method known to those of ordinary skill in the art, and may be comprised of other suitable materials, including polymers such as poly(methylmethacrylate), although silica capillaries generally are preferred.

The open tubular capillary may be used to separate the components of complex chemical mixtures by transporting the complex chemical mixture through the capillary, applying a voltage across the capillary under conditions conductive to capillary electrochromatography, thereby causing the different components to move through the apparatus at different speeds based on the components affinities to the different compounds within the PEMs, resulting in the separation of the components of the complex chemical mixture.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

The invention claimed is:

1. A method for the detection and separation of enantiomers in a complex chemical mixture using capillary electrophoresis with mass spectrometry comprising contacting the complex chemical mixture with a micelle comprising at least two surfactant molecules of the formula:

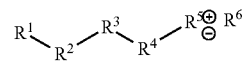

wherein $R^1$ is a functionality group, $R^2$ is a hydrophobic tail, $R^3$ is a linker, $R^4$ is a chiral selector, $R^5$ is a head group comprising a sulfate or a sulfonate, and $R^6$ is a counterion, wherein the functionality group is polymerized with at least one other surfactant molecule in the micelle; and separating enantiomers in the complex chemical mixture using capillary electrophoresis with mass spectrometry, wherein the detection and separation of enantiomers occurs at a pH from about 1.5 to about 5.5.

2. The method of claim 1, wherein
the functionality group comprises an alkynyl or alkenyl group;
the hydrophobic tail comprises an alkyl group;
the linker comprises an amide, carbamate, or ureido group;
the chiral selector comprises an amino acid or amino acid derivative; and
the counterion comprises an alkali, $Li^+$, $Na^+$, $K^+$, $Rb^+$, $Cs^+$, $Mg^+$, $NH_4^+$, $Cu^{+2}$, $Zn^{+2}$, $(CH_3)_4N^+$, $(C_2H_5)_4N^+$, $(C_3H_7)_4N^+$, $(C_4H_9)_4N^+$), or quaternary ammonium.

3. The method of claim 2, wherein the amino acid or amino acid derivative is selected from the group consisting of aspartic acid, arginine, glycine, glutamic acid, proline, threonine, theanine, cysteine, cystine, alanine, valine, phenylalanine, tyrosine, leucine, isoleucine, asparagine, serine, lysine, histidine, tryptophan, ornithine, methionine, carnitine, aminobutyric acid, glutamine, hydroxyproline, taurine, morvaline, sarcosine, amino methanesulfonic acid, and combinations thereof.

4. The method of claim 1, wherein the detection and separation of enantiomers occurs at a pH from about 2 to about 3.

5. The method of claim 1, wherein the complex chemical mixture comprises negatively charged racemic analytes.

6. The method of claim 1, wherein the complex chemical mixture comprises neutral analytes.

7. The method of claim 1, wherein the complex chemical mixture comprises positively charged racemic analytes.

* * * * *

UNITED STATES PATENT AND TRADEMARK OFFICE
CERTIFICATE OF CORRECTION

PATENT NO. : 8,168,440 B2
APPLICATION NO. : 11/692602
DATED : May 1, 2012
INVENTOR(S) : Shahab Ahmed Shamsi and Syed Asad Ali Rizvi It is certified that error appears in the above-identified patent and that said Letters Patent is hereby corrected as shown below:

At column 28, line 32, delete "$(C_2{}^+H_5)_4N^+$," after $(CH_3)_4N^+$," and insert --$(C_2H_5)_4N^+$,--.

Signed and Sealed this
Nineteenth Day of June, 2012

David J. Kappos
*Director of the United States Patent and Trademark Office*